US 7,122,638 B2

(12) United States Patent
Rodman

(10) Patent No.: US 7,122,638 B2
(45) Date of Patent: Oct. 17, 2006

(54) MONOCLONAL HUMAN NATURAL ANTIBODIES

(75) Inventor: Toby C. Rodman, New York, NY (US)

(73) Assignee: The Institute for Human Genetics and Biochemistry, Geneva (CH)

( * ) Notice: Subject to any disclaimer, the term of this patent is extended or adjusted under 35 U.S.C. 154(b) by 673 days.

(21) Appl. No.: 10/247,946

(22) Filed: Sep. 20, 2002

(65) Prior Publication Data
US 2003/0144485 A1 Jul. 31, 2003

Related U.S. Application Data

(62) Division of application No. 09/462,118, filed as application No. PCT/US98/25258 on Nov. 24, 1998, now Pat. No. 6,610,833.

(60) Provisional application No. 60/066,464, filed on Nov. 24, 1997.

(51) Int. Cl.
*C12P 21/08* (2006.01)

(52) U.S. Cl. .............................. 530/388.1; 530/388.35; 530/809

(58) Field of Classification Search ...................... None
See application file for complete search history.

(56) References Cited

U.S. PATENT DOCUMENTS

| 4,997,764 A | 3/1991 | Dalla Favera |
| 5,606,026 A | 2/1997 | Rodman |
| 5,656,272 A | 8/1997 | Le et al. |

FOREIGN PATENT DOCUMENTS

WO WO-93/22349 A1 11/1993

OTHER PUBLICATIONS

Hua Liu, et al., "Production of anti-tumor human monoclonal antibodies using different approaches", Human Antibodies and Hybridomas, Jan. 1993, vol. 4, pp. 2-8.
Kari Siemoneit, et al., "Isolation and Epitope Characterization of Human Monoclonal Antibodies to Hepatitis C Virus Core Antigen", Hybridoma, Feb. 1994, vol. 13, No. 1, pp. 9-13.
Karen Dahl, et al., "Differences among Human Immunodeficiency Virus Strains in Their Capacities to Induce Cytolysis or Persistent Infection of a Lymphoblastoid Cell Line Immortalized by Epstein-Barr Virus," Journal of Virology, May 1987, vol. 61, No. 5, pp. 1602-1608.
Michelle S. Glasky, et al., "Stability of Specific Immunoglobulin Secretion by EBV-Transformed Lymphoblastoid Cells and Human-Murine Heterohybridomas", Hybridoma, Aug. 1989, vol., 8, No. 4, pp. 377-389.

Almond, N.M. and J.L. Heeney. 1998. Aids vaccine development in primate models, *Aids* 12: (suppl.A) S133.
Bendelac, A. and D.T. Fearon, 1997. Innate immunity. Innate pathways that control acquired immunity. *Curr. Opinion Immunol.* 9:1-3.
Cao,Y.et al. 1995. Virologic and immunologic characterization of long-term survivors of humna immunodeficiency virus type 1 infection. *New Eng.J.Med.* 332:201-208.
Carroll, M.C. et al. 1998. Linkages of innate and adaptive immunity. *Curr. Opinion Immunol.* 10:36-40.
Chen, P., M.Mayne, C. Power and A.Nath. 1997. The Tat protein of HIV-1 induces tunor necrosis factor alpha production. Implications for HIV-associated neurologic diseases. *J. Biol. Chem.* 272:22385-22388.
Coutinho, A. et al., 1995. Natural antibodies. *Curr. Opinion Immunol.* 7:812-818.
Crouau-Roy, B., et al. 1996. A fine-scale comparison of the human and chimpanzee genomes: linkage disequilibrium and sequences analysis. *Hum. Mol. Genet.* 5:1131-1137.
Cullen, B.R. 1991. Regulation of human immunodeficiency virus replication. *Ann.Rev. Microbiol.* 45:219-250.
Donahue, R.E., et al. 1998. Reduction in SIV replication in rhesus macaques infused with autologous lymphocytes engineered with antiviral genes. *Nat. Med.* 4:181-186.
Ehret, A., et al. 1996. Resistance of chimpanzee T cells to human immunodeficiency virus type 1 Tat-enhanced oxidative stress and apoptosis. *J. Virol.* 10:6502-6507.
Frankel, A.D. et al. 1988. Cellular uptake of the tat protein from human immunodeficiency virus. *Cell* 55:1189-1193.
Frankel, A.D., et al. 1989. Activity of synthetic peptides from the Tat protein of human immunodeficiency virus type 1. *Proc.Natl.Acad. Sci. USA.* 86:7397-7401.
Ghandi, R.T. et al. 1998. HIV-1 directly kills CD4+ T cells by a Fas-independent mechanism. *J.Exp.Med.* 187:1113-1122.
Gougeon, M.L., et al. 1996. Comparative analysis of apoptosis in HIV-infected humans and chimpanzees: relation with lymphocyte activation. *Immunol. Lett.* 51:75-81.
Heilman, C.A. et al. 1998. HIV vaccines—Where are we going? *Nat. Med.* 4:532-534.
Herbein, G., et al. 1998. Distinct mechanisms trigger apoptosis in human immunodeficiency virus type 1-infected and in uninfected bystander T Iymphocytes. *J. Virol.*72:660-670.
Hulskotte, E.G.J, et al. 1998. Towards and HIV vaccine: lessons from studies in macaque models. *Vaccine* 16:904-915.

(Continued)

*Primary Examiner*—G. R. Ewoldt
(74) *Attorney, Agent, or Firm*—Darby & Darby

(57) ABSTRACT

Disclosed herein are hydridoma cell lines producing monoclonal human natural IgM antibodies and methods of use thereof. The antibodies are the monoclonal equivalents of circulating human natural antibodies. Also disclosed herein are pharmaceutical formulations and methods for treating HIV-1 infected individuals using the monoclonal human natural antibodies.

5 Claims, 11 Drawing Sheets

OTHER PUBLICATIONS

Iida, T., et al. 1998. Fas antigen expression and apoptosis of lymphocytes in macaques infected with simian immunodeficiency virus strain mac. *Arch. Virol.* 143:717-729.

Janeway, C.R.Jr. 1998. Presidential address to the American Association of Immunologists. The road less traveled by: the Role of innate immunity in the adaptive immune response. *J. Immunol.* 161:539-544.

Klein, L., e tal. 1998. $CD^4$ T cell tolerance to human C-reactive protein, an inducible serum protein, is mediated by medullary thymic epithelium. *J.Exp.Med.* 188:5-16.

Kuppuswamy, M., et al. 1989. Multiple functional domains of Tat, the trans-activator of HIV-1, defined by mutational analysis. *Nucl. Acids Res.* 17:3551-3561.

Matzinger, P, 1994. Tolerance, danger and the extended family. *Ann Rev. Immunol.* 12:991-1045.

McCune, J.M. Animal models of HIV-1 disease. 1997. *Science* 279:2141-2142.

Medzhitov, R. et al. 1997. Innate immunity: impact on the adaptive immune response. *Cur. Opinion Immunol.* 9:4-9.

Mohri, H., et al. 1998. Rapid turnover of T lymphocytes in SIV infected rhesus macaques. *Science* 279:1223-1227.

Montefiori, D.C., et al. 1996. Neutralizing and infection-enhancing antibody responses to human immunodeficiency virus type 1 in long-term nonprogressors. *J.Infect.Dis.* 173:60-67.

New, D.R., et al. 1997. Human immunodeficiency virus type 1 Tat protein induces death by apoptosis in primary neuron cultures. *J. Neurovirol.* 168-173.

Noraz,N., et al. 1997. HIV-induced apoptosis of activated primary CD4+ T lymphocytes is not mediated by Fas-Fas ligand, AIDS 11:1671-1680.

Novembre,F.J., et al. 1997. Development of AIDS in a chimpanzee infected with human immunodeficiency virus type 1 infected with human immunodeficiency virus type 1. *J. Virol.* 71:4086-4091.

Parker, W., et al.1996. Isohemagglutinins and xenoreactive antibodies. Members of a distinct family of natural antibodies. *Human. Immunol.* 45:94-104.

Rodman, T.C., et al. 1997. innate natural antibodies. Primary roles indicated by specific epitopes. *Human Immunol.* 55:87-95.

Rosenzweig, M., et al. 1998. Increased rates of CD4+ and CD8+ T lymphocyte turnover in simian immunodeficiency virus-infected macaques. *Proc. Natl. Acad. Sci. USA.* 95:6388-6393.

Samuelsson,A., et al. 1997. Apoptosis of CD4 and CD19+ cells during human immunodeficiency virus type-1 infection—correlation with clinical progression, viral loas and loss of humoral immunity. *Virology* 238:180-188.

Steinman, R.M. et al. 1998. Antigen presentation and related immunological aspects of HIV-1 vaccines. *AIDS* 12:(suppl.A) S97-S112.

Taylor, M.D., et al. 1998. Interferon treatment inhibits the replication of simian immunodeficiency virus at an early stage: evidence for a block between attachment and reverse transcription. *Virology* 241:156-162.

Van Parijs, L. et al. 1998. Homeostasis and self-tolerance in the immune system: turning lymphocytes off. *Science* 280:243-248.

Vives, E., et al. 1997. A truncated HIV-1 Tat protein basic domain repidly translocates through the plasma membrane and accumulates in the cell nucleus. *J. Biol. Chem .* 272:16010-16017.

Wessenlingh, S.L., et al. 1997. Cellular localization of tumor necrosis factor mRNA in neurological tissue from HIV-infected patients by combined reverse transcription/polymerase chain reaction in situ hybridization and immunohistochemistry. *J.Neuroimmunol.* 74: 1-8.

Chiorazzi N, et al. Use of Epstein-Barr virus-transformed B-cell lines for the generation of immunoglobulin-producing human B cell hybridomas. *J Exp Med* 156:930-935, 1982.

Aitken R.J., Fertilization and early embryogenesis. In Hillier SG, Kitchener HC, Neilson JP, Eds. Scientific Essentials of Reproductive Medicine. London: W.B.Saunders, p219-229, 1996.

Atherton D., et al. Routine protein sequence analysis below ten picomoles: one sequencing facility's approach. p. 409-418,1993, Techniques in Protein Chem IV.

Baker E.N. et al., Three-dimensional structure of lactoferrin in various functional states. *Adv Exp Med Biol 357*:1-12, 1994.

Beavis RC, Chait BT. High-accuracy molecular mass determination of proteins using matrix-assisted desorption mass spectrophotometry. *Anal Chem 62*:1836-1840, 1990.

Bi By, et al., Internalization of human lactoferrin by the Jurkat human lymphoblastic T cell line. *Eur J Cell Biol 69*:288-296, 1996.

Boyden SV. Natural antibodies and the immune response. *Adv Immunol 5*:1-28, 1966.

Chiorazzi N, Generation of stable autoantibody-secreting B cell hybridomas. *Mol Biol Reports 16*:65-73, 1992.

Westergren,I. and B.B.Johansson. 1993. Altering the blood-brain barrier in the rat by intacarotid infusion of polycations: A comparison between protamine, poly-L-lysine and poly-Larginine. *Acta Physiol. Scand.* 149:99.-104.

Concar D, The jaws of lactoferrin. *Nature 344*:710, 1990.

Fleet JC. A new role for lactoferrin: DNA binding and transcription activation. *Nutr Rev 53*:226-231, 1995.

Friesen AD, et al., Column ion exchange preparation and characterization of an Rh immune globulin (WinRho) for intravenous use. *J Applied Biochem.* 3:164-175, 1981.

Garre C, et al., Lactoferrin binding sites and nuclear localization in K562(S) cells. *J. Cell Physiol 153*:477-482, 1992.

Gerstein M, et al., Two hinges produce a see-saw motion between alternative close-packed interfaces. *J Mol Biol 234*:357-372, 1993.

Guilbert B, et al., Naturally occurring antibodies against nine common antigens in human serum. Detection, isolation and characterization. *J Immunol 128*:2779-1787, 1982.

Haas GG Jr, et al., Antisperm antibodies and infertility. *Reproductive Immunology.* Mass. Blackwell Science. part 2, Chapt. 7, 1996, pp. 717-211.

He J, et al., Sequence specificity and transcriptional activation in the binding of lactoferrin to DNA. *Nature 373*:721-724, 1995.

Hutchens et al., Origin of intact lactoferrin and its DNA-binding fragment found in the urine of milk-fed infants. Evaluation of stable isotopic enrichment, *Ped Res 29*:243-250, 1991.

Jamil K, et al., Induction of acrosomal reaction in sperm with ionophore A23187 and calcium. *Arch. Androl 7*:293-292, 1981.

Lonnerdal et al., Lactoferrin: molecular structure and biological function. *Ann Rev Nutr 15*:93-110, 1995.

Metz-Boutigue et al., Human lactoferrin: amino acid sequence and structural comparisons with other transferrin. *Eur J Biochem 145*:659-676, 1984.

Nonchev et al., Protamine-histone replacement and DNA replication in the male mouse pronucleus. *Mol. Reprod. Devel 25*:72-76, 1990.

Pruslin et al., Caveats and suggestions for the ELISA. *J Immunol Meth 137*:27-35, 1991.

Rodman et al., Turnover of basic chromosomal, proteins in fertilized eggs: a cytoimmunochemical study of events in vivo. *J. Cell Biol 90*:351-361, 1981.

Schagger H, van Jagow G. Tricine-sodium dodecyl sulfate-polyacrilamide gel electrophoresis for the separation of proteins in the range from 1 to 100 kDa. *Anal Biochem. 166*:368-373, 1987.

Spik et al., Primary and three-dimensional structure of lactotransferrin (lactoferrin) glycans. *Adv Exp Med Biol 357*:21-32, 1994.

Yee et al., Contraceptive vaccine formulations with sperm proteins. *Reproductive immunology.* Mass. Blackwell Science. part 2, chapt. 33, 1996.

Rodman et al., Protamine-reactive natural antibodies in human sera. *J Exp Med 167*: 1228-1246, 1988.

Manchester et al., Lactoferrin-Reactive Natural Antibodies, Annals New York Acad. of Sciences, 815:475 (1997).

Lachgar et al., Repair of the in Vitro HIV-1-Induced Immunosuppression and Blockade of the Generation of Functional Suppressive CD8 Cells by Anti-Alpha Interferon and Antit-Tat Antibodies, Biomed & Pharmacother. 50:13-18 (1996).

Brocke et al., Treatment of Experimental Encephalomyelitis With a Peptide Analogue of Myelin Basic Protein, Nature 379:343-46 (1996).

Re et al., Effect of Antibody to HIV-1 Tat Protein on Viral Replication in Vitro and Progression of HIV-1 Disease in Vivo, J. Acq. Imm. Def. Syndromes and Human Retrovir. 10:408-416 (1995).

Friedman et al., Predicting Molecular Interactions and Inducible Complementarity: Fragment Docking of Fab-Peptide Complexes, Proteins: Structure, Function and Genetics 20:15-24 (1994).

Coffman et al. Mechanism and Regulation of Immunoglobulin Isotype Switching, Advances in Immuno. 54:229-70 (1993).

Rodman et al., Human Immunodeficiency Virus (HIV) Tat-Reactive Antibodies Present in Normal HIV-Negative Sera and Depleted in HIV-Positive Sera. Indentification of the Epitope, J. Exp. Med. 175:1247-53 (1992).

Varela et al., Population Dynamics of Natural Antibodies in Normal and Autoimmune Individuals, Proc. Natl. Acad. Sci. USA 88:5917-21 (1991).

Avrameas, Natural Autoantibodies: From 'Horror Autotoxicus' to 'Gnothi Seauton', Goday 12:154-160 (1991).

Urlacher et al., IgM Anti-Idiotypes That Block Anti-HLA Antibodies: Naturally Occurring or Immune Antibodies?, Clin. Exp. Immunol. 83:116-120 (1991).

Rodman et al., Identification of a Low-Affinity Subset of Protamine-Reactive IgM Antibodies Present in Normal, Deficient in AIDS, SERA: Implications of HIV Latency, Cl. Immun. and Immunopath. 57:430-440 (1990).

Posner et al., The Construction and Use of a Human-Mouse Myeloma Analogue Suitable for the Routine Production of Hybridomas Secreting Human Monoclonal Antibodies, Hybridoma 6:611-625 (1987).

Muñoz et al., New Experimental Criteria for Optimization of Solid-Phase Antigen Concentration and Stability in Elisa, J. Immuno. Methods 94:137-144 (1986).

Rodman et al., Naturally Occurring Antibodies Reactive With Sperm Proteins: Apparent Deficiency in AIDS SERA, Science 228:1211-15 (1985).

Rodman et al., p15, A Nuclear-Associated Protein of Human Sperm: Identification of Four Variants and Their Occurrence in Normal and Abnormal Seminal Cells, Gamete Research 8:129-47 (1983).

Goodman et al., Immunological Identification of Lactoferrin as a Shared Antigen on Radioiodinated Human Sperm Surface and in Radioiodinated Human Seminal Plasma, J. Repro. Immuno, 3:99-108 (1981).

Hekman et al., The Antigens of Human Seminal Plasma (With Special Reference to Lactoferrin as a Spermatozoa-Coating Antigen), Protides Biol. Fluids 16:549 (1969).

FIG. 5

1. MEPVDPRLEPWK
2. LEPWKHPGSQPK
3. GSQPKTACTNCY
4. CTNCYCKKCCFH
5. KCCFHCQVCFIT
6. VCFITCALGISY
7. LGISYGRKKRRQ
8. GRKKRRQRRRPP
9. KKRRQRPRRPQG
10. RPPQGSQTHQVS
11. THQVSLSKQPTS
12. KQPTSQRGDPTE

```
SEQUENCE LISTING

<160> NUMBER OF SEQ ID NOS: 36

<210> SEQ ID NO 1
<211> LENGTH: 12
<212> TYPE: PRT
<213> ORGANISM: Human

<400> SEQUENCE: 1

Met Glu Pro Val Asp Pro Arg Leu Glu Pro Trp Lys
 1               5                  10

<210> SEQ ID NO 2
<211> LENGTH: 12
<212> TYPE: PRT
<213> ORGANISM: Human

<400> SEQUENCE: 2

Leu Glu Pro Trp Lys His Pro Gly Ser Gln Pro Lys
 1               5                  10

<210> SEQ ID NO 3
<211> LENGTH: 12
<212> TYPE: PRT
```

<213> ORGANISM: Human

<400> SEQUENCE: 3

Gly Ser Gln Pro Lys Thr Ala Cys Thr Asn Cys Tyr
1               5                   10

<210> SEQ ID NO 4
<211> LENGTH: 12
<212> TYPE: PRT
<213> ORGANISM: Human

<400> SEQUENCE: 4

Cys Thr Asn Cys Tyr Cys Lys Lys Cys Cys Phe His
1               5                   10

<210> SEQ ID NO 5
<211> LENGTH: 12
<212> TYPE: PRT
<213> ORGANISM: Human

<400> SEQUENCE: 5

Lys Cys Cys Phe His Cys Gln Val Cys Phe Ile Thr
1               5                   10

<210> SEQ ID NO 6
<211> LENGTH: 12
<212> TYPE: PRT
<213> ORGANISM: Human

<400> SEQUENCE: 6

Val Cys Phe Ile Thr Cys Ala Leu Gly Ile Ser Tyr
1               5                   10

<210> SEQ ID NO 7
<211> LENGTH: 12
<212> TYPE: PRT
<213> ORGANISM: Human

<400> SEQUENCE: 7

Leu Gly Ile Ser Tyr Gly Arg Lys Lys Arg Arg Gln
1               5                   10

<210> SEQ ID NO 8
<211> LENGTH: 12
<212> TYPE: PRT
<213> ORGANISM: Human

<400> SEQUENCE: 8

Gly Arg Lys Lys Arg Arg Gln Arg Arg Arg Pro Pro
1               5                   10

<210> SEQ ID NO 9
<211> LENGTH: 12
<212> TYPE: PRT
<213> ORGANISM: Human

<400> SEQUENCE: 9

Lys Lys Arg Arg Gln Arg Pro Arg Pro Gln Gly
1               5                   10

<210> SEQ ID NO 10
<211> LENGTH: 12
<212> TYPE: PRT
<213> ORGANISM: Human

```
<400> SEQUENCE: 10

Arg Pro Pro Gln Gly Ser Gln Thr His Gln Val Ser
 1               5                  10

<210> SEQ ID NO 11
<211> LENGTH: 12
<212> TYPE: PRT
<213> ORGANISM: Human

<400> SEQUENCE: 11

Thr His Gln Val Ser Leu Ser Lys Gln Pro Thr Ser
 1               5                  10

<210> SEQ ID NO 12
<211> LENGTH: 12
<212> TYPE: PRT
<213> ORGANISM: Human

<400> SEQUENCE: 12

Lys Gln Pro Thr Ser Gln Arg Gly Asp Pro Thr Glu
 1               5                  10

<210> SEQ ID NO 13
<211> LENGTH: 12
<212> TYPE: PRT
<213> ORGANISM: Human

<400> SEQUENCE: 13

Asp Lys Val Glu Arg Leu Lys Gln Val Leu Leu His
 1               5                  10

<210> SEQ ID NO 14
<211> LENGTH: 12
<212> TYPE: PRT
<213> ORGANISM: Human

<400> SEQUENCE: 14

Lys Gln Val Leu Leu His Gln Gln Ala Lys Phe Gly
 1               5                  10

<210> SEQ ID NO 15
<211> LENGTH: 12
<212> TYPE: PRT
<213> ORGANISM: Human

<400> SEQUENCE: 15

Gln Gln Ala Lys Phe Gly Arg Asn Gly Ser Asp Cys
 1               5                  10

<210> SEQ ID NO 16
<211> LENGTH: 12
<212> TYPE: PRT
<213> ORGANISM: Human

<400> SEQUENCE: 16

Arg Asn Gly Ser Asp Cys Pro Asp Lys Phe Cys Leu
 1               5                  10

<210> SEQ ID NO 17
<211> LENGTH: 12
<212> TYPE: PRT
<213> ORGANISM: Human

<400> SEQUENCE: 17
```

```
Pro Asp Lys Phe Cys Leu Phe Gln Ser Glu Thr Lys
 1               5                  10
```

<210> SEQ ID NO 18
<211> LENGTH: 12
<212> TYPE: PRT
<213> ORGANISM: Human

<400> SEQUENCE: 18

```
Phe Gln Ser Glu Thr Lys Asn Leu Leu Phe Asn Asp
 1               5                  10
```

<210> SEQ ID NO 19
<211> LENGTH: 12
<212> TYPE: PRT
<213> ORGANISM: Human

<400> SEQUENCE: 19

```
Asn Leu Leu Phe Asn Asp Asn Thr Glu Cys Leu Ala
 1               5                  10
```

<210> SEQ ID NO 20
<211> LENGTH: 12
<212> TYPE: PRT
<213> ORGANISM: Human

<400> SEQUENCE: 20

```
Asn Thr Glu Cys Leu Ala Arg Leu His Gly Lys Thr
 1               5                  10
```

<210> SEQ ID NO 21
<211> LENGTH: 12
<212> TYPE: PRT
<213> ORGANISM: Human

<400> SEQUENCE: 21

```
Arg Leu His Gly Lys Thr Thr Tyr Glu Lys Tyr Leu
 1               5                  10
```

<210> SEQ ID NO 22
<211> LENGTH: 12
<212> TYPE: PRT
<213> ORGANISM: Human

<400> SEQUENCE: 22

```
Thr Tyr Glu Lys Tyr Leu Gly Pro Gln Tyr Val Ala
 1               5                  10
```

<210> SEQ ID NO 23
<211> LENGTH: 12
<212> TYPE: PRT
<213> ORGANISM: Human

<400> SEQUENCE: 23

```
Gly Pro Gln Tyr Val Ala Gly Ile Thr Asn Leu Lys
 1               5                  10
```

<210> SEQ ID NO 24
<211> LENGTH: 12
<212> TYPE: PRT
<213> ORGANISM: Human

<400> SEQUENCE: 24

```
Gly Ile Thr Asn Leu Lys Lys Cys Ser Thr Ser Pro
 1               5                  10
```

-continued

<210> SEQ ID NO 25
<211> LENGTH: 12
<212> TYPE: PRT
<213> ORGANISM: Human

<400> SEQUENCE: 25

Lys Cys Ser Thr Ser Pro Leu Leu Glu Ala Cys Glu
 1               5                  10

<210> SEQ ID NO 26
<211> LENGTH: 12
<212> TYPE: PRT
<213> ORGANISM: Human

<400> SEQUENCE: 26

Ser Pro Leu Leu Glu Ala Cys Glu Phe Leu Arg Lys
 1               5                  10

<210> SEQ ID NO 27
<211> LENGTH: 12
<212> TYPE: PRT
<213> ORGANISM: Human

<400> SEQUENCE: 27

Ser Leu Asp Gly Gly Tyr Val Tyr Thr Ala Cys Lys
 1               5                  10

<210> SEQ ID NO 28
<211> LENGTH: 12
<212> TYPE: PRT
<213> ORGANISM: Human

<400> SEQUENCE: 28

Val Tyr Thr Ala Cys Lys Cys Gly Leu Val Pro Val
 1               5                  10

<210> SEQ ID NO 29
<211> LENGTH: 12
<212> TYPE: PRT
<213> ORGANISM: Human

<400> SEQUENCE: 29

Cys Gly Leu Val Pro Val Leu Ala Glu Asn Tyr Lys
 1               5                  10

<210> SEQ ID NO 30
<211> LENGTH: 12
<212> TYPE: PRT
<213> ORGANISM: Human

<400> SEQUENCE: 30

Leu Ala Glu Asn Tyr Lys Ser Gln Gln Ser Ser Asp
 1               5                  10

<210> SEQ ID NO 31
<211> LENGTH: 12
<212> TYPE: PRT
<213> ORGANISM: Human

<400> SEQUENCE: 31

Ser Gln Gln Ser Ser Asp Pro Asp Pro Asn Cys Val
 1               5                  10

```
<210> SEQ ID NO 32
<211> LENGTH: 12
<212> TYPE: PRT
<213> ORGANISM: Human

<400> SEQUENCE: 32

Pro Asp Pro Asn Cys Val Asp Arg Pro Val Glu Gly
1               5                   10

<210> SEQ ID NO 33
<211> LENGTH: 12
<212> TYPE: PRT
<213> ORGANISM: Human

<400> SEQUENCE: 33

Asp Arg Pro Val Glu Gly Tyr Leu Ala Val Ala Val
1               5                   10

<210> SEQ ID NO 34
<211> LENGTH: 12
<212> TYPE: PRT
<213> ORGANISM: Human

<400> SEQUENCE: 34

Tyr Leu Ala Val Ala Val Val Arg Arg Ser Asp Thr
1               5                   10

<210> SEQ ID NO 35
<211> LENGTH: 12
<212> TYPE: PRT
<213> ORGANISM: Human

<400> SEQUENCE: 35

Val Arg Arg Ser Asp Thr Ser Leu Thr Trp Asn Ser
1               5                   10

<210> SEQ ID NO 36
<211> LENGTH: 12
<212> TYPE: PRT
<213> ORGANISM: Human

<400> SEQUENCE: 36

Ser Leu Thr Trp Asn Ser Val Lys Gly Lys Lys Ser
1               5                   10
```

MONOCLONAL HUMAN NATURAL ANTIBODIES

This application is a divisional of U.S. patent application Ser. No. 09/462,118, filed Dec. 28, 1999, now U.S. Pat. No. 6,610,833, issued Aug. 26, 2003, which is a 371 of PCT/US98/25258, filed Nov. 24, 1998, which claims the benefit of priority of U.S. Provisional Application No. 60/066,464, filed Nov. 24, 1997.

BACKGROUND OF THE INVENTION

The effector molecules of the immune system include a repertoire of circulating immunoglobulins non-attributable to exogenous antigenic induction, variously referred to as "autoantibodies" or "natural antibodies". The existence of such antibodies has been long recognized and their various proposed functions may be classed as "self-attack" or "self-benefit". For the former, the specter of autoimmunity is raised and the term "autoantibodies" is customarily applied. For the latter, the term "autoantibodies" is customarily applied. For the latter, designated "natural; antibodies", support of homeostasis is implied.

U.S. patent application Ser. No. 08/271,210 filed Jul. 5, 1994, discloses a circulating natural human antibody immunoreactive with an arginine-rich epitope present on human protamine. U.S. Pat. No. 5,606,026 issued Feb. 25, 1997, discloses that the arginine-rich epitope is present in the Tat protein of HIV-1 and further discloses a second circulating human natural antibody immunoreactive with a different epitope on the Tat protein of HIV-1. In addition, a third circulating human natural antibody immunoreactive with a cryptic epitope present on human lactoferrin is disclosed therein.

It has been shown that all three of the above-mentioned circulating human natural antibodies decrease after HIV infection reaching minimal levels as the patient progresses to AIDS. These antibodies are found in all sera of normal humans of all ages, from cord blood to adult, which, by virtue of their ubiquitous occurrence, are identified as natural antibodies.

Therefore, what is needed in the art are the monoclonal counterparts of these circulating human natural antibodies for their therapeutic and diagnostic uses.

SUMMARY OF THE INVENTION

The present invention provides monoclonal forms of human natural antibodies.

In one aspect, the present invention provides hybridoma cell line RWL-1 (ATCC CRL 12431), a product of the fusion of Epstein Barr virus (EBV) transformed umbilical cord blood cells and HMMA, mouse: human heteromyeloma cells.

In another aspect, the present invention provides monoclonal human IgM antibodies, produced by RWL-1 cells.

In yet another aspect, the present invention provides another hybridoma cell line, RWT-4 (ATCC CRL 12472), a product of the fusion of EBV-transformed umbilical cord cells with SHM-D33 cells (ATCC CRL 1668), mouse: human heteromyeloma cells.

In yet another aspect, the present invention provides monoclonal human IgM antibodies produced by RWT-4 cells.

In a still further aspect, the present invention provides hybridoma cell line RWT-12 (ATCC CRL 12477), a product of the fusion of EBV-transformed human umbilical cord cells and HMMA, mouse: human heteromyleoma cells.

In a still further aspect, the present invention provides monoclonal human IgM antibodies produced by RWT-12 cells.

In a still further aspect, the present invention provides a method for treating a patient suffering from an infection caused by HIV-1 comprising administering to a patient in need of such treatment an effective amount for treating said infection of a monoclonal antibody selected from the group consisting of antibodies produced by RWT-4 cells, RWT-12 cells, and mixtures thereof.

In a still further aspect, the present invention provides a method for increasing CD4+T cells in a patient suffering from an infection caused by HIV-1 comprising administering an amount for increasing CD4+T cells of antibodies produced by hybridoma cells having Accession Nos. ATCC CRL 12472, ATCC CRL 12477 and mixtures thereof.

In a still further embodiment, the present invention provides a pharmaceutical formulation comprising isolated human IgM monoclonal antibodies selected from the group consisting of antibodies produced by hybridoma cell lines having Accession Nos. ATCC CRL 12472, ATCC CRL 12477, mixtures thereof and a pharmaceutical acceptable vehicle.

These and other aspects of the present invention will be apparent to those of ordinary skill in the art in light of the present description, claims and drawings.

BRIEF DESCRIPTION OF THE DRAWINGS

FIG. 5. Sequences of the 12—amino acid peptides representing the Tat protein of HIV-1. Peptides 1–7 (SEQ ID NOS: 1 to 7) and 9–12 (SEQ ID NOS: 9 to 12) represent 5 residue overlaps. Peptide 8 (SEQ ID NO: 8) was included to provide another variant of arginine distribution in order to ascertain the maximum reactivity of human sera attributable to the arginine-rich region of Tat. Maximum titer with the arginine-rich region (peptides 7,8,9, SEQ ID NOS: 7, 8, 9) was, in fact, displayed with peptide 8 (SEQ ID NO: 8). Maximum titer with the cysteine-rich region (peptides 4,5, SEQ ID NOS: 4, 5) was displayed with peptide 4 (SEQ ID NO 4).

A. IgM

B. IgG Analysis of reactivity of two cohorts of 70 human sera, HIV+ and HIV– (normal), with Tat protein of HIV. The HIV+ cohort was assembled from sera collected prior to 1994, therefore the characteristics are not attributable to the anti-HIV medications in use since that time. Each assay plate included both HIV+ and HIV– specimens and a single normal serum (ST). The recorded titer for each serum (X) represents X/ST.

The titers are grouped in intervals of 10 with the number of sera of each cohort designated for each interval. The distributions of both IgM and IgG titers for the HIV+ sera are skewed to the lower intervals, particularly those of the IgM.

Figure 7A:
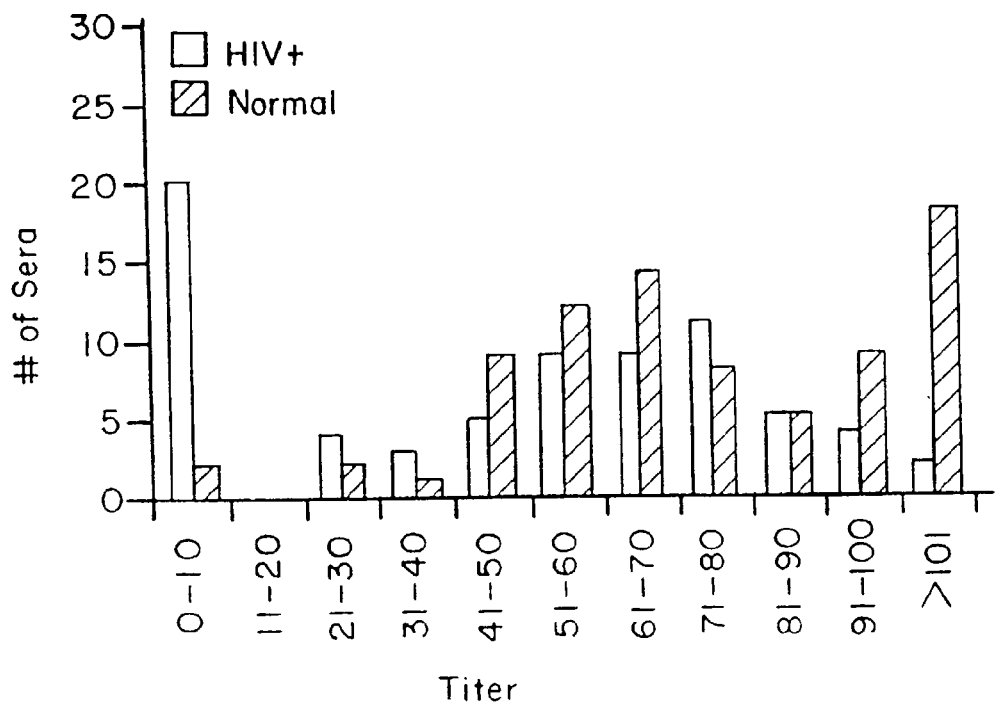
Figure 7B:
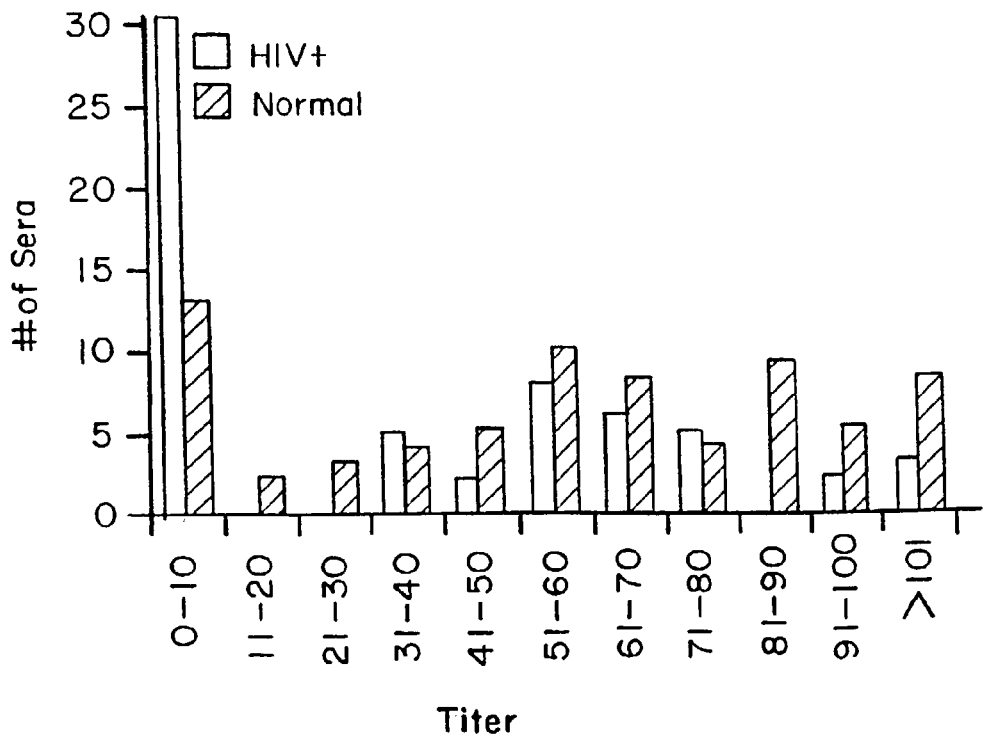

FIG. 7(A and B). Distribution of titers of A.IgM and B.IgG, reactive with peptide 8 (SEQ ID NO: 8) (FIG. 5) in each of two cohorts of 70 human sera, HIV+ and HIV– (normal). The preponderance of low, or no titers of IgM and, even more strikingly, of IgG in the HIV+ sera indicates that depletion of the natural antibody reactive with the arginine-rich sequence of Tat is a correlation of the pathoprogression of HIV.

Figure 8A:
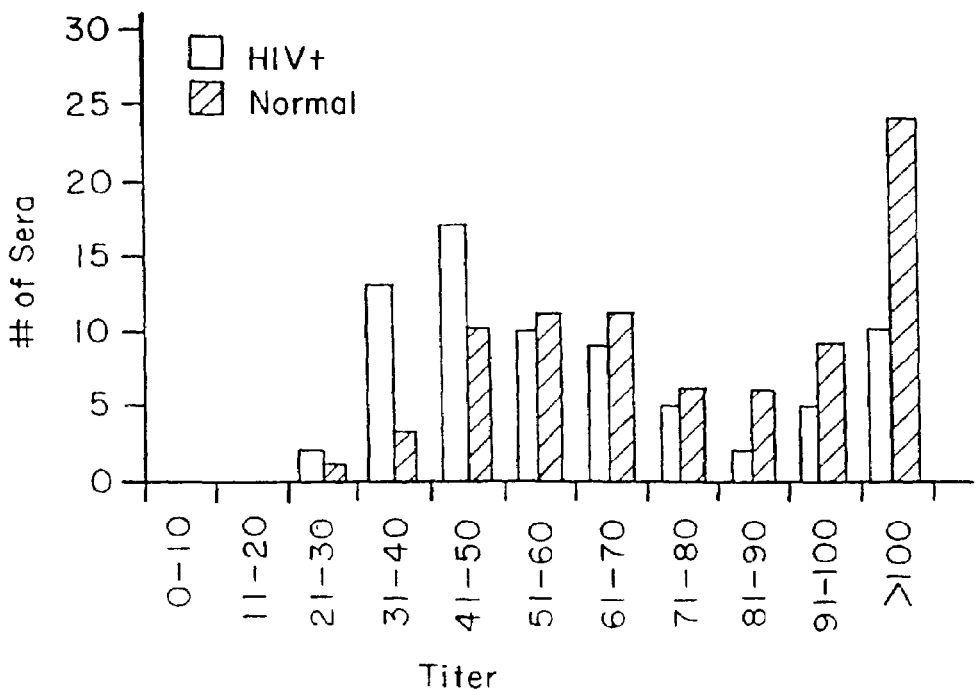
Figure 8B:
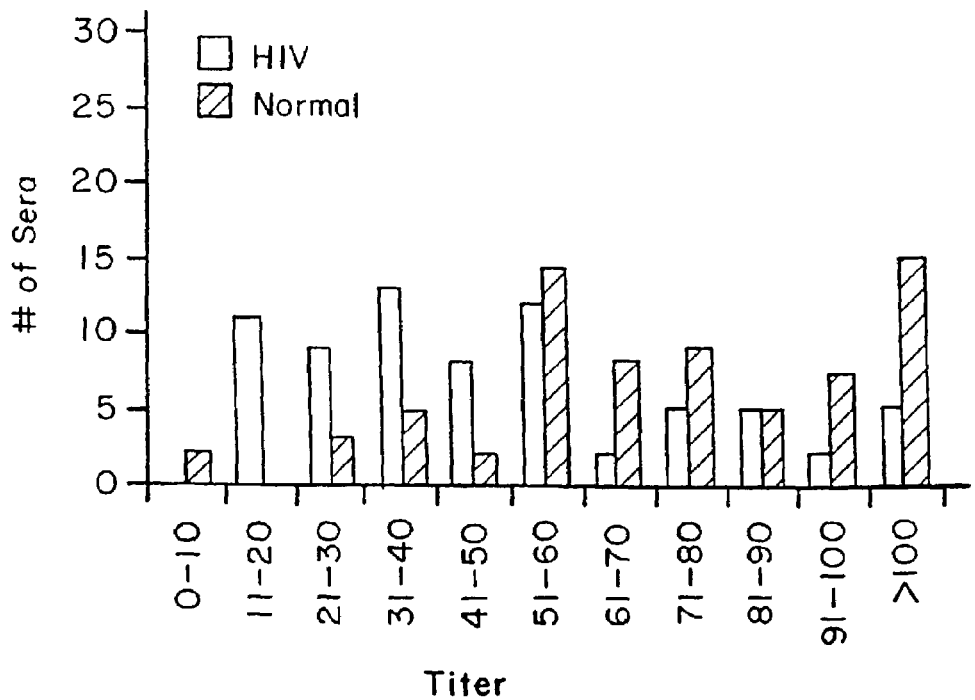
Figure 11A:
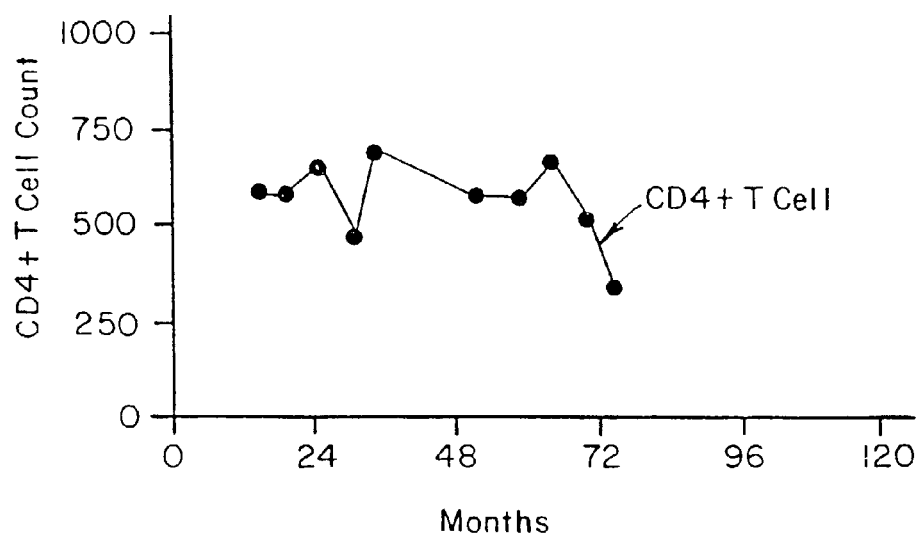
Figure 11B:
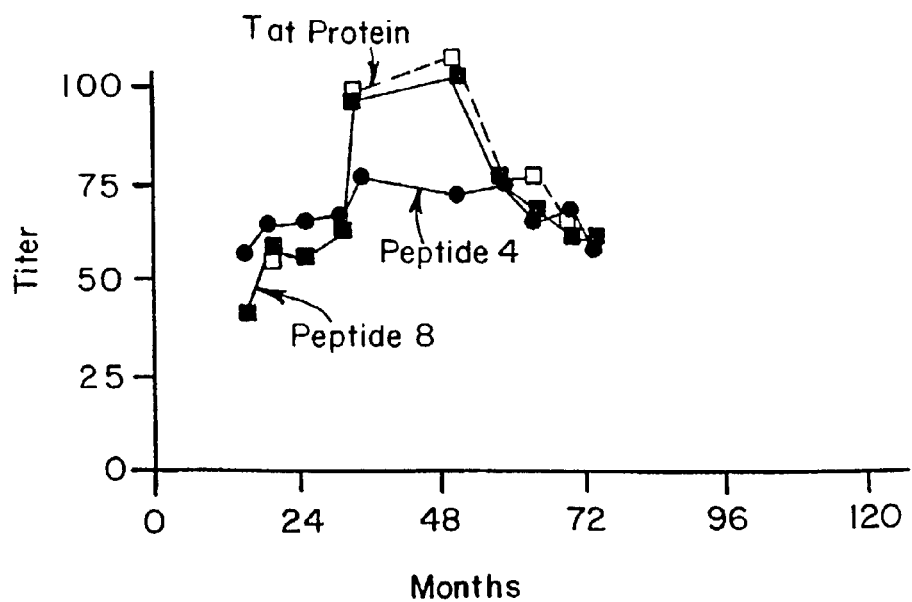

FIG. 8(A and B). The distribution of titers of A. IgM and B. IgG reactivity with peptide 4 (SEQ ID NO: 4) (FIG. 5) in two cohorts of 70 human sera, HIV+ and HIV– (normal), is in accord with the general trend of lower titers, in HIV+ sera, of the total Tat-reactive antibodies, but less stringent than that demonstrated for the titers of the peptide 8 (SEQ ID NO: 8) reactive antibodies (FIG. 11).

FIG. 9(A and B).

A. CD4+T cell counts.

B. Titers of IgM reactivity with Tat protein, peptide 4 (SEQ ID NO:4) and peptide 8 (SEQ ID NO: 8) (FIG. 5) of serial specimens from an HIV+ male over a period of five years preceding his death with a diagnosis of AIDS. Each specimen for CD4+T cell count was obtained at the same time as that for serum analysis. The correlation of drop in CD4+T cells with the decline of titers of the natural antibodies is particularly marked with respect to the titer of peptide 8 (SEQ ID NO: 8) reactive antibodies, supporting the proposition that the decline in that natural antibody may allow the T cell apoptosis, attributed to Tat, to proceed.

FIG. 10(A and B).

A. CD4+T cell count.

B. Titers of IgM antibodies reactive with Tat protein, peptide 4 (SEQ ID NO:4) and peptide 8 (SEQ ID NO: 8) (FIG. 5) in serial specimens of sera, collected over a period of 9 years, from an HIV+ male whose duration of infection is estimated at over 11 years, but has displayed no HIV associated pathology and has had no anti-HIV medication. Each specimen for serum analysis was obtained at the same time as that for CD4+ cell count. The titers and pattern of maintenance of titers of the natural antibodies are correlative with maintenance of the CD4+T cell counts within the normal range.

FIG. 11(A and B).

A. CD4+T cell count.

B. Titers of IgM reactive with Tat protein, peptide 4 (SEQ ID NO: 4) and peptide 8 (SEQ ID NO: 8) (FIG. 5) of serial specimens from an HIV+ male. Following the report of specimen 4, in which decline of CD4+T cell count was noted, anti-HIV therapy was initiated. The count in specimen 5, taken after 6 months of therapy showed significant rise and the titer of IgM reactive with peptide 8, (SEQ ID NO: 8) underwent an exceedingly high rise. The successive specimens then showed maintenance of CD4 T cell counts and natural antibody titers, concomitant with generally good clinical status.

DETAILED DESCRIPTION OF THE INVENTION

All patents, patent applications and literature references cited herein are hereby incorporated by reference in their entirety.

In one preferred embodiment, the present invention provides a monoclonal form of a human, natural IgM antibody immunoreactive with a crytic epitope present on human lactoferrin. This antibody is produced by hybridoma RWL-1, deposited with the American Type Culture collection (Manassas, Va.) on Nov. 14, 1997 and received ATCC Accession No. ATCC CRL-12431. The hybridoma was produced by fusing an Epstein Barr virus transformed human umbilical cord cell with a mouse: human heteromyeloma cell as described in Example 1 below. The hybridoma produces human monoclonal antibodies of the IgM isotype. The fact that the antibody producing cell (the human umbilical cord cell) is of neonate origin and the antibody is of the IgM isotype (and therefore does not cross the placenta) demonstrates that this is indeed a natural antibody.

The IgM antibody immunoreactive with lactoferrin is characterized as a natural antibody identified since it has been shown to be present in a large cohort of normal human sera, and for which no pathologic role or association is apparent. The reactive site for this natural antibody has been shown previously (3) and confirmed here, to be present in the plasma membrane complex of the human sperm head. These studies, designed to establish the molecular identity of that reactive site, have confirmed that an approximately 72.6 kD protein present in seminal plasma (2), accurately determined here as 80 kD, is also present in the protein coat of the sperm head and that 80 kD protein is homologous with, and in fact is, lactoferrin. It is shown herein that the noted natural antibody is specifically reactive with LF in a configuration other than that of the LF ubiquitous in body fluids. That configuration and the natural antibody reactivity is revealed, in vitro (FIGS. 2, 4), following denaturation of native circulating LF, and is revealed, in vivo (FIG. 3) in the LF incorporated in the protein coat of the human sperm head. LF is present in seminal plasma in the native configuration and, by a mechanism not yet determined, the antibody recognition form is assumed when it is deposited in the spermatozoal membrane/coat complex. The transition to that form and deposition in the sperm surface coat presumably take place during the period of spermatogenic maturation in the seminiferous tubules of the testes. It is relevant, therefore, to note that large molecules such as immunoglobulins, particularly IgM, are excluded from the lumina of the seminiferous tubules (24) and, therefore, from immunoreactivity with sperm components during spermiogenesis. That barrier, however, does not exist in the female reproductive tract, where the full complement of circulating antibodies is present (23). Therefore, the LF reactive natural antibody is available for immunoreactivity with the LF of the sperm coat, following ejaculation into the female reproductive tract. That interaction may take place in the sperm coat in situ as shown (FIG. 3) and is definitely capable of taking place with the LF released, along with other coat and plasma membrane components (FIG. 4) as the sperm undergoes the sequence of capacitation and acrosome reaction, which facilitate passage of the sperm through the protective zona pellucida surrounding the oocyte, and subsequent entry into the oocyte (9, 10). Since the acrosome reaction involves fusion of the acrosomal membrane with the plasma membrane, the components of the overlying protein coat are dispersed. Thus, the released LF could have ready access to the ooplasm were it not for the presence, in the fertilization milieu, of the natural antibody capable of immunological nullification of the ability of that LF to endocytose through the oocyte membrane and, subsequently, to interact with the DNA of the gametes or pronuclei.

Among the many functions and interactions defined for LF, its capacity to be endocytosed and interact with DNA is of increasing interest (7, 8, 27–29). Particularly interesting are the recent reports that the interaction of LF with DNA is marked by sequence specificity (7). The underlying molecular bases for that specificity have not been defined, but it is reasonable to expect that if LF/DNA interaction occurs, in vivo it does so within a defined control system. It is logical, also, to propose that such a system exists in the organized chromosomal complement of somatic cells, but not in the nascent undifferentiated complements of the pronuclei. Thus, in that context, the postulated control of sequence specificity in interaction of LF with DNA may not be operative. The presence of a natural antibody selectively reactive with LF in the specific configuration in which it exists in the sperm coat, but not with LF in its ubiquitous circulating form, may represent a fortuitous natural selection mechanism on two bases: (1) inhibition of LF interaction with the DNA complements of the fertilized oocyte and (2) restriction of immunoreaction by the circulating natural antibody with LF at other loci, in its more prevalent, important function-serving forms. The innate occurrence of that natural antibody is verified since the hybridoma secreting the Mab, utilized to provide significant data of this study, was derived from a human cord blood B cell.

As shown below in Example 2, the antibody is immunoreactive with an epitope present on human lactoferrin, specifically the form of lactoferrin present in the protein coat of the human sperm head. Lactoferrin is an 80 kD glycoprotein present in the sperm head. Following induction of the acrosome reaction occurring during fertilization, lactoferrin (which has been shown to interact with and bind to DNA) could potentially interfere with the interaction of sperm and oocyte DNA. Therefore, one of the uses of the antibody of the present invention is as an additive to in vitro fertilization reactions in order to prevent lactoferrin from interacting with sperm DNA prior to fertilization.

In alternative, preferred embodiments of the present invention, hybridoma cells producing monoclonal IgM antibodies immunoreactive with the Tat protein of HIV-1 are provided. The hybridoma cell lines RWT-4 and RWT-12 are immunoreactive with peptide 4 (SEQ ID NO: 4) and peptide 8 (SEQ ID NO: 8), respectively, of FIG. 5. These hybridoma cells, as is the case with hybridoma RWL-1, were produced by fusing EBV-transformed human umbilical cord cells with mouse:human heteromyeloma cells. RWT-4 cells were deposited with the ATCC on Feb. 12, 1998 and received Accession No. ATCC CRL 12472 and RWT-12 cells were deposited on Feb. 25, 1998 with the ATCC and received Accession No. ATCC CRL 12477. The epitope specificity of each antibody is shown below in Example 3.

The monoclonal IgM antibodies produced by hybridomas RWL-1 (ATCC CRL 12341) RWT-4 (ATCC CRL 12472) and RWT-12 (ATCC CRL 12477) can be isolated from cultures of the cells that produce them and purified using techniques known to those of ordinary skill in the art, such as ammonium sulfate precipitation, HPLC, column chromatography, etc.

The antibodies of the present invention are the monoclonal equivalents of the circulating IgM antibody identified in *Science* 228:1211, 1985 (for RWL-1 cells) and described in U.S. Pat. No. 5,606,026 issued Feb. 20, 1997 (for RWT-4 and RWT-12 cells). These circulating antibodies are deficient in HIV-infected individuals and decrease as AIDS approaches. Therefore, the monoclonal antibodies produced by ATCC CRL 12341, ATCC CRL 12477 and ATCC CRL 12472 can be used as positive controls in assays for prognosing the onset of AIDS.

In another preferred embodiment of the invention, a method for treating a patient suffering from an infection caused by HIV-1 comprising administering an effective amount to treat HIV-1 of natural human IgM antibodies selected from the group consisting of antibodies produced by RWT-4 cells, antibodies produced by RWT-12 cells and mixtures thereof. It is envisioned that replenishment of the natural antibodies deficient in HIV-1-infected and AIDS patients will be of clinical benefit to these individuals.

As shown below in Example 5, the Tat protein of HIV-1 does not stimulate the induction of antibodies in humans (see Table I of Example 5). This observation coupled with the fact that long term survivors (LTS)/long term non-progressors (LTNP), patients who are HIV-1 positive but who do not exhibit any symptoms of the disease or progress to AIDS, have normal levels of the circulating natural antibodies equivalent to the IgM antibodies produced by the hybridomas of the present invention. This demonstrates the utility of administering the monoclonal antibodies of the present invention as a therapeutic to treat the disease. Due to the fact that the Tat protein of HIV-1 has such an important role in establishing and maintaining infection, and that the protein does not appear to be immunogenic in humans, administration of the monoclonal antibodies of the present invention to infected individuals is one way to introduce antibodies specifically directed against the Tat protein.

The data of FIGS. 9, 10 and 11 clearly establish a correspondence, in HIV+ humans, between the CD4+T cell count and the serum titer of the two IgM natural antibodies reactive with the Tat protein of HIV, specifically with the sequences of the protein represented by peptide 4 (SEQ ID NO: 4) and peptide 8 (SEQ ID NO: 8) (FIG. 10). The correspondence is more sharply shown with the antibody reactive with peptide 8 (SEQ ID NO: 8), representing the arginine-rich sequence of Tat.

Each of FIGS. 9, 10 and 11 display a unique example of that correspondence. FIG. 9 shows the clinical report of CD4+T cell count and the antibody assay data of a series of corresponding serum specimens from an HIV+ male over a period of 5 years preceding his death with a diagnosis of AIDS. FIG. 10 displays the corresponding data of specimens from an HIV+ male whose duration of infection is estimated at over 11 years, but who has displayed no HIV-associated pathology and has had no anti-HIV medication. FIG. 11 displays the data of specimens from an HIV+ male showing that, following institution of anti-HIV medication, both CD4+T cell count and titers of Tat reactive antibodies, particularly the antibody reactive with peptide 8, rose to levels within the normal range.

Since various Intravenous IgG (IVIG) preparations currently commercially available (e.g., from Sandoz Pharmaceuticals or Cutter Biological) have been tested and certified for parenteral administration, an IVIG preparation may be used as a vehicle for administration of the monoclonal IgM antibodies of the present invention. These preparations have been shown to be safe for human parenteral administration.

Generally, the dosage administered will, of course, vary depending upon known factors such as age, health and weight of the recipient, type of concurrent treatment, frequency of treatment, etc. Usually, a dosage of active ingredient can be between about 0.001 and about 10 milligrams per kilogram of body weight. Precise dosage, frequency of administration and time span of treatment should be monitored, for each individual, by determination of rise in CD4+T cell count and other clinical indicia of relief from pathogenetic progression.

In yet another preferred embodiment, a method for increasing CD4+T cell counts in a patient is provided comprising administering to a patient in need of such treatment, an effective amount to increase CD4+T cell counts of antibodies selected from the group consisting of antibodies produced by hybridoma ATCC CRL 12472, ATCC CRL 12477 and mixtures thereof. The effective amounts are the same as mentioned above.

For parenteral administration, the antibodies of the present invention can be formulated into pharmaceutical formulations or dosage forms as a solution, suspension, emulsion, or lyophilied powder in association with a pharmaceutically acceptable parenteral vehicle. Examples of such vehicles are water, saline, Ringer's solution, dextrose and 5% human serum albumin. In addition, as mentioned above, IVIG commercially available preparations can be used as vehicles for delivery of the antibodies of the present invention.

The pharmaceutical formulations of the present inventions do not need to constitute an effective amount of the antibodies of the present inventions since such amounts can be achieved by administering a plurality of such formulations.

The present invention is further described below in specific example which are intended to further describe the invention without limiting its scope.

EXAMPLE 1

The hybridoma, RWL-1, which secretes the monoclonal human IgM antibody reactive with a defined cryptic sequence of human lactoferrin, was created by fusion of a human umbilical cord blood B cell with the cell line HMMA, a human/mouse heteromyeloma (Posner M R, Ellorim H, Santos D. (1987) *Hybridoma* 6:611.) as set forth below.

Figure 2A:
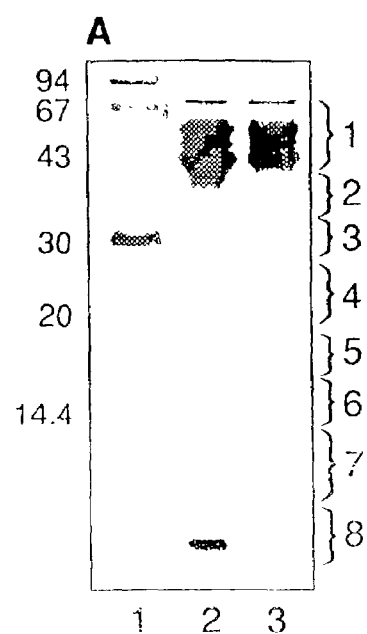
FIG. 2(A-C) is an Tricine SDS Page.
  A. Protein stain. 1 mol. wt. markers; 2 LF(M); 3 SP80 (acidic and basic). Resolution of fraction 7 shows 2 distinct bands.
  B. Immunotransfer with normal human male serum showing reactivity specifically localized in fraction 7B.
  C. Immunoreactivity with fraction 7B of a monoclonal antibody (Mab) IgM from a human B cell derived hybridoma.
Figure 2B:
Figure 2C:

The cord blood was obtained, at caesarian section, from a normal (but otherwise non-identified) neonate and the mononuclear cells were isolated by density gradient centrifugation using FICOLL-PAQUE® (available from Pharmacia of Peapack, N.J.). The collected cells were washed with RPMI-1640 medium (Sigma) and added to a culture of Epstein-Barr Virus (EBV), (obtained from cultures of ATCC CRL 1612 cells) in RPMI 1640 medium and incubated (37° C.) for 2 hours. The cells were then spun down, resuspended in RPMI 1640, supplemented with fetal calf serum (FCS), cyclosporin A, Pen/Strep (10 units Penicillin/100 mg Streptomycin per ml), and plated in 96 well plates at 30 cells/well. After 5 weeks incubation at 37° C. with periodic medium replenishment, the culture medium of each well was tested by ELISA (Pruslin F H, Winston R, Rodman Tc. (1991) *J. Immunol. Meth.* 137:27) for the IgM monoclonal antibody (Mab) specifically reactive with the 7B fraction of denatured lactoferrin (FIG. 2C).

Selected cultures of EBV immortalized B cells were grown to a cell concentration of $10^6$ cells/well, then washed 5× in RPMI-1640 (non-supplemented). The fusion partner (HMMA cells, described in Posner, M. R., et al., *Hybridoma* 6:, 611, 1987) were grown in RPMI 1640, FCS, Pen/Strep and azaguanine, and washed 3× in non-supplemented RPMI-1640° $10^6$ cells were mixed with an equal number of the EBV immortalized cells. The mixed cell culture was spun, supernatant decanted and the cells resuspended in warm (37° C.) 40% polyethylene glycol/RPMI-1640 (pH 7.2) and held for one minute. The cells were spun, washed 2× with RPMI, pH 7.8, then resuspended ($10^6$ cells/ml) in HY medium (Sigma), supplemented with 20% FCS, HAT (Sigma), ouabain, Pen/Strep and plated out at $10^5$ cells/well. After 3 weeks the growth positive wells were tested for the presence of the specific antibody. The contents of the wells with positive antibody were limited out (diluted) and replated at 0.5 cells/well in HY/HT (Sigma), and supplemented with 20% FCS, SPIT (Sigma), Pen/Strep. The cells were grown for 5 weeks (37° C.) and the contents of each well were retested for Mab specificity. Selected cultures were incubated and grown to density of $10^6$ cells/ml. and spun at 400 RPM, 5 min. Each cell pellet was suspended in 5 ml 80% FCS, 10% DMSO and 10% RPMI-1640 and stored frozen at −70° C., in 2 ml aliquots. Stored aliquots have been defrosted and retested for viability and antibody specificity.

The hybridoma was deposited on Nov. 14, 1997 with the American Type Culture Collection (Rockville, Md.) and received ATCC Accession No. ATCC CRL 12431.

EXAMPLE 2

In the Example set forth below, the following Materials and Methods were used.

LF Proteins

Human milk lactoferrin, obtained from Sigma (L3770) is designated LF (M). Seminal plasma LF was isolated from pooled specimens of semen, from clinically normal volunteer donors. Following liquefaction, sperm-free plasma was obtained by centrifugation and separated by DEAE ion exchange chromatography (11) into a pool of basic and a pool of acidic fractions. Each pool was subjected to gel filtration SEPHACRYL™ S 300 HR, available from Amersham Pharmacia of Piscataway, N.J., and the first fraction of each pool was resolved at 80 kD and designated SP80-basic and SP80-acidic, respectively.

Cyanogen Bromide (CNBr) Cleavage and SDS PAGE

Figure 1A:
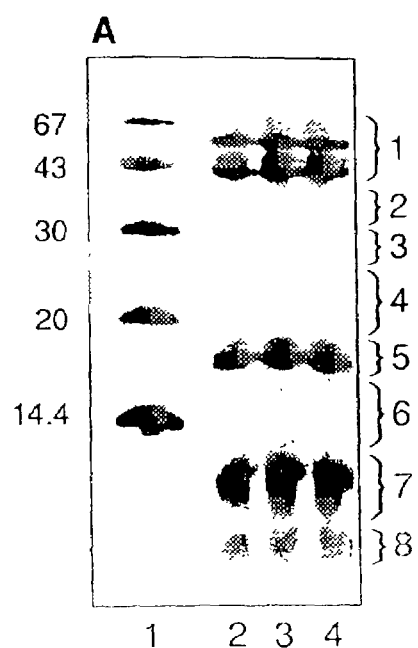
FIG. 1(A-C) is an SDS PAGE of cyanogen bromide [CNBR] cleaved lactoferrin (LF) and SP80.
  A. Protein stain. 1 mol. wt. markers; 2 LF(M); 3 SP80-basic; 4 SP80-acidic. All three proteins (2,3,4) show identical cleavage fractions 1–8.
  B. Immunotransfer with serum of rabbit immunized with SP80 (acidic and basic) showing multiplicity of reactive sites and homology of reactivity of LF(M) and SP80.
  C. Immunotransfer with normal human male serum showing reactivity solely with fraction 7 of each of the 3 proteins.
Figure 1B:
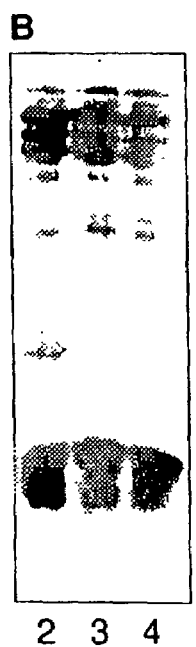
Figure 1C:
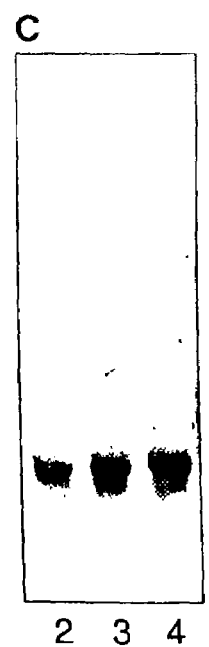

CNBr treatment of SP80-basic, SP80-acidic and LF(M) was carried out as described (12). Briefly, a 10 mg/ml 70% formic acid solution of each protein was incubated with CNBr (200 fold molar excess) at room temperature for 18–24 hr. Following lyophilization, the cleavage mixtures were electrophoresed on an SDS polyacrylamide gel (FIG. 1). For enhanced resolution of the low molecular weight fractions (FIG. 2) electrophoresis was carried out on a 16.5% tricine gel (13).

Characterization of Fraction 7B

Fraction 7B was excised from the gel and extracted with H20-SDS was precipitated by addition of KC1 and the component peptides of 7B were purified by dialysis against PBS (pH 7.2). Untreated sperm-free seminal plasma proteins and native LF were PBS solutions. Determination that LF fraction 7B consisted of two peptides was carried out by the Laboratory of Mass Spectrometry at Rockefeller University, utilizing matrix-associated laser desorption/ionization mass spectrometry (14). N-terminal sequencing of the peptides of LF fraction 7B was carried out by the Protein Sequencing Facility at Rockefeller University, utilizing repeated cycles of Edman degradation followed by PTH analysis with microbore HPLC (15).

Immunoreactivity

Western blot was performed on Immobilon-P (Millipore) transfers of the electropherograms of LF(M) and acidic and basic SP80 and visualized by chemiluminescence. ELISA was carried out by standardized methodology (16–18). Sera were those of a rabbit immunized with human LF(M), a rabbit immunized with SP80 (acidic and basic combined) and human sera selected at random from a group of discards from clinical laboratories, identified by gender, age and "no clinical findings". Reactivity by all human sera was solely with fraction 7 of the PAGE (FIG. 1) and resolved at a distinct band designated 7B (FIG. 2).

Monoclonal Antibody (Mab) Specific for Fraction 7B

Mononuclear cells were isolated from cord blood of a normal neonate by density gradient centrifugation using FICOLL-PAQUE® (Pharmacia) and transformed with Epstein-Barr virus (19). Fusion with the parental cell line HMMA, utilizing standard procedures (20), resulted in a set of IgM secreting hybridomas for which monoclonality was established by limiting dilution. Since reactivity of serum with denatured milk LF(M) and SP80 was confined to a single PAGE fraction (FIG. 2) that fraction was isolated from the gel and utilized, together with a set of proteins and peptides for which specific reactivity by other human natural antibodies has been established (16,18), as antigens in ELISA to screen those Mab's for exclusive reactivity with fraction 7B.

Cytologic Localization of LF/SP 80 in Sperm Heads.

Figure 3A:
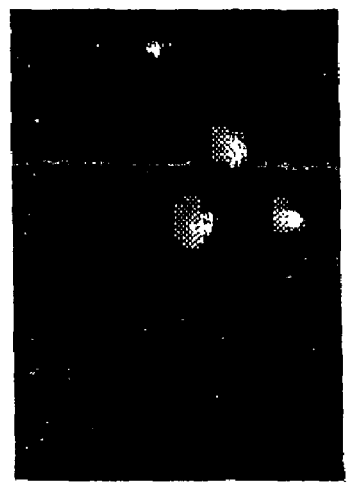
FIG. 3(A and B) shows in situ immunoreactivity, displayed by FITC labeled anti-human IgM, of a component of human sperm heads with: (A) human serum; (B) Mab reactive with LF fraction 7B.
Figure 3B:
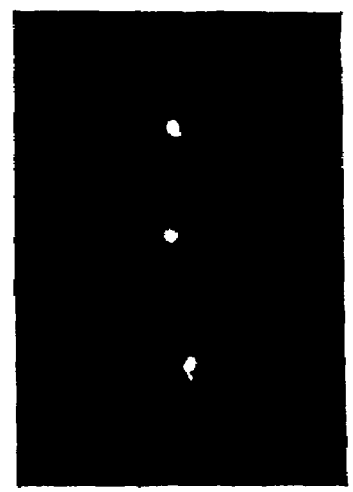

A fraction of swim-up human sperm was obtained from spontaneously liquefied seminal plasma, washed 3 times with PBS, and finally suspended in either human serum diluted 1:500 in PBS or in PBS solution of the purified Mab, followed by overnight incubation at 40° C. Each suspension was washed 3 times with PBS and the collected sperm incubated in FITC labeled anti-human IgM (Sigma) for 1 hour. The sperm were washed with PBS, and a drop of the suspension placed on a slide, examined and photographed, utilizing FITC-specific filters (FIG. 3).

Sperm Coat Protein Fraction

Figure 4:
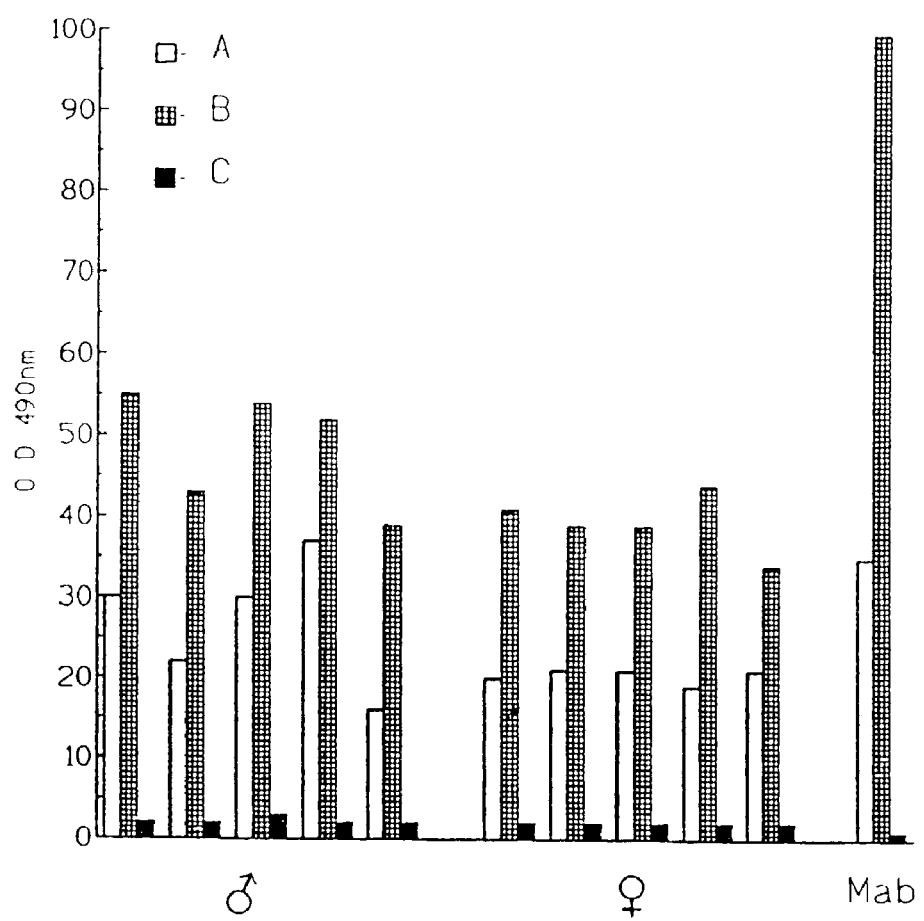
FIG. 4(A-C) shows reactivity, by ELISA, of serum (diluted 1:100) of each of 5 males, 5 females and the Mab with: (A) 10 µg/ml of the complement of sperm coat proteins released following induction of the acrosome reaction in a suspension of swim-up spermatozoa; (B) 10 µg/ml of purified fraction 7B LF(M); C. 10 µg/ml native (non-denatured) LF(M). The relative reactivities of A. and B. indicate that a serum antibody and the Mab are reactive with a specific component, but not all, of the sperm coat complement. The lack of reactivity with native LF (C) verifies that the natural antibody of serum and the Mab are reactive with a site of LF that is not revealed in its native state.

A fraction containing the components of the sperm coat was obtained by induction of the acrosome reaction (21) in a suspension of spermatozoa: the swim-up sperm were gently washed with PBS, collected and suspended in Ca medium: 2 mM $CaCl_2$ 10 mM ionophore A23187 (Calbiochem), 1 mM PMSF (Sigma) and incubated 4 hr at room temperature. The sperm cells were pelleted by low speed centrifugation and the resultant supernatant cleared of particles by high speed centrifugation followed by dialysis overnight at 40° C. The supernatant was tested by ELISA, for reactivity with human sera and with the Mab reactive with LF fraction 7B (FIG. 4).

Results

The data reported here confirm previous studies indicating that an 80 kD protein of human seminal plasma is homologous with LF (1,2). Fractionation of sperm-free seminal plasma by DEAE ion exchange chromatography (not shown) confirmed that the 80 kD protein is present in two forms: basic and acidic, which contains the glycan moiety (22). CNBr cleavage fractions on SDS gels were identical for both forms of SP80 as well as for LF derived from human milk (FIGS. 1A,2A). Also, the pattern of immunoreactivity of those fractions with serum of a rabbit immunized with SP80 (FIG. 1) or with LF from human milk (not shown), are correspondingly identical. Similarly, prior reports (4) that normal human sera show no immunoreactivity with native LF from milk or with SP80 isolated from, or in the context of, seminal plasma are confirmed (FIG. 4). Especially significant is the confirmation (FIGS. 1, 2) that a natural antibody, identified in normal human sera (3,4), is reactive with a cryptic sequence of LF and SP80 that is revealed upon denaturation of those proteins (FIGS. 1, 2). That sequence is segregated in fraction 7B from the PAGE of CNBr cleavage products of LF(M) and SP80 (FIG. 2). The innate occurrence of the natural antibody is strikingly demonstrated by the derivation of a hybridoma from a cord blood cell which secretes an IgM/K that is specifically reactive with a component of fraction 7B (FIGS. 2, 4).

Mass Spectrometry revealed that fraction 7B contains 2 peptides, 10 kD and 9 kD. N-terminal sequencing identified DKVER (amino acid positions 1–5 of SEQ ID NO: 13) for the load major peptide and SLDGG (amino acid positions 1–5 of SEQ ID NO: 27) for the 9 kD peptide. Upon the assumption that CNBr cleavage of LF is at methionine residues and by reference to the published structure of LF (12) the sequence of each of the 2 peptides was derived and localized to the C lobe. A set of 12 residue peptides, with 5 residue overlaps, comprising the derived linear sequences of the 2 peptides, was created (Table I). Thus far, specific reactivity of human serum IgM has not been identified with any one of those peptides tested singly, indicating that the fundamental epitope for the natural antibody, although embodied in LF fraction 7B, is conformation dependent.

The localization of that epitope, in situ in the sperm head, is demonstrated by cyto-immunoreactivity of human serum and by the Mab specifically reactive with LF(M)/SP80 fraction 7B (FIG. 3) Further evidence that LF is present in the sperm coat proteins, in that configuration in which the natural antibody epitope is revealed, is provided by FIG. 4. Following induction of the acrosome reaction (21), resulting in dispersion of the protein coat/plasma membrane ensemble overlying the acrosomal region of the sperm head, reactivity of a component of the coat with human serum IgM and with the Mab was shown (FIG. 4). Thus, FIGS. 3,4 provide evidence that, following the sequence of capacitation and acrosome reaction, in vivo the LF shed from the sperm coat may be available for entry into the sperm-penetrated oocyte. However, since the complete immunoglobulin repertoire of plasma is present in the female reproductive tract (23) that availability may be inhibited by the natural antibody.

TABLE I

Overlapping duodecapeptides comprising the components of LF fraction 7B. A. 10 kD, B. 9 kD

| A. | Seq. ID No: | B. | Seq. ID No: |
|---|---|---|---|
| D K V E R L K Q V L L H | 13 | S L D G G Y V Y T A C K | 27 |
| K Q V L L H Q Q A K F G | 14 | V Y T A C K C G L V P V | 28 |
| Q Q A K F G R N G S D C | 15 | C G L V P V L A E N Y K | 29 |
| R N G S D C P D K F C L | 16 | L A E N Y K S Q Q S S D | 30 |
| P D K F C L F Q S E T K | 17 | S Q Q S S D P D P N C V | 31 |
| F Q S E T K N L L F N D | 18 | P D P N C V D R P V E G | 32 |
| N L L F N D N T E C L A | 19 | D R P V E G Y L A V A V | 33 |
| N T E C L A R L H G K T | 20 | Y L A V A V V R R S D T | 34 |
| R L H G K T T Y E K Y L | 21 | V R R S D T S L T W N S | 35 |
| T Y E K Y L G P Q Y V A | 22 | S L T W N S V K G K K S | 36 |
| G P Q Y V A G I T N L K | 23 | | |
| G I T N L K K C S T S P | 24 | | |
| K C S T S P L L E A C E | 25 | | |
| S P L L E A C E F L R K | 26 | | |

As noted (Results) reactivity of human serum IgM or of the Mab was not displayed against any of the peptides, indicating that the epitope is conformational.

REFERENCES

1. Hekman A, Rumke P. The antigens of human seminal plasma (with special reference to lactoferrin as a spermatozoa-coating antigen). *Protides Biol Fluids* 16:549–552, 1969.
2. Goodman S A, Young L G. Immunological identification of lactoferrin as a shared antigen on radioiodinated sperm surface and in radioiodinated human seminal plasma. *J. Reprod Immunol* 21:99–108, 1981.
3. Rodman T C, Laurence J, Pruslin F H, Chiorazzi N, Winston R. Naturally occurring antibodies reactive with sperm proteins: apparent deficiency in AIDS sera. *Science* 228:1211–1215, 1985.
4. Manchester K, Winston R., Rodman T C. Lactoferrin-reactive natural antibodies. *Ann NY Acad Sci in press*.
5. Boyden S V. Natural antibodies and the immune response. *Adv Immunol* 5:1–28, 1965.
6. Guilbert B, Dighiero G, Avrameas S. Naturally occurring antibodies against nine common antigens in human serum. Detection, isolation and characterization. *J Immunol* 128:2779–1787, 1982.
7. He J, Furmanski P. Sequence specificity and transcriptional activation in the binding of lactoferrin to DNA. *Nature* 373:721–724, 1995.
8. Bi B Y, Liu J L, Legrand D, Roche A-C, Capron M, Spik G, Mazurier J. Internalization of human lactoferrin by the Jurkat human lymphoblastic T cell line. *Eur J Cell Biol* 69:288–296, 1996.
9. Yanagimachi R. Mammalian fertilization. In: Knobil E, Neil J D, Eds. The Physiology of Reproduction. New York: Raven Press, p 189–317, 1994.
10. Aitken R J. Fertilization and early embryogenesis. In Hillier S G, Kitchener H C, Neilson J P, Eds. Scientific Essentials of Reproductive Medicine. London: W. B. Saunders, p 2.10, 1996.
11. Friesen A D, Bowman J M, Price H W. Column ion exchange preparation and characterization of an Rh immune globulin for intravenous use. *J Applied Biochem.* 3:164–175, 1981.
12. Metz-Boutigue M-H, Joll&s J, Mazurier J, Schoentgen F, Legrand D, Spik G, Montreuil J, Joll&s P. Human lactoferrin: amino acid sequence and structural comparisons with other transferrin. *Eur J Biochem* 145:659–676, 1984.
13. Schagger H, van Jagow G. Tricine-sodium dodecyl sulfate-polyacrilamide gel electrophoresis for the separation of proteins in the range from 1 to 100 kDa. *Anal Biochem.* 166:368–373, 1987.
14. Beavis R C, Chait B T. High accuracy molecular mass determination of proteins using matrix-assisted desorption mass spectrophotometry. *Anal Chem* 62:1836–1840, 1990.
15. Atherton D, Fernandez J, DeMott M, Andrews L, Mische S M. Routine protein sequence analysis below ten picomoles. In: Angeletti R H, Ed. Techniques in Protein Chemistry IV, Calif. Academic Press. p 409–418,1993.
16. Rodman T C, Pruslin F H, Chauhan Y, To S E, Winston R. Protamine-reactive natural antibodies in human sera. *J Exp Med* 167:1228–1246, 1988.
17. Pruslin F H, To S E, Winston R, Rodman T C. Caveats and suggestions for the ELISA. *J Immunol Meth* 137: 27–35, 1991.
18. Rodman T C, To S E, Hashish H, Manchester K. Epitopes for natural antibodies of human immunodeficiency virus (HIV)-negative and HIV-positive sera are coincident with two key functional sequences of HIV Tat protein. *Proc Natl Acad Sci USA* 90:7719–7723, 1993.

19. Chiorazzi N, Wasserman R L, Kunkel H G. Use of Epstein/Barr virus transformed B-cell lines for the generation of immunoglobulin-producing human B cell hybridomas. *J Exp Med* 156:930–935, 1982.
20. Chiorazzi N, Generation of stable autoantibody-secreting B cell hybridomas. *Mol Biol Reports* 16:65–73, 1992.
21. Jamil K, White I G, Induction of acrosomal reaction in sperm with ionophore A23187 and calcium. *Arch Androl* 7:293–292, 1981.
22. Spik G, Coddeville B, Mazurier J, Bourne Y, Cambillant C, Montreuil J. Primary and three-dimensional structure of lactotransferrin (lactoferrin) glycans. *Adv Exp Med Biol* 357:21–32, 1994.
23. Yee A J, Silver L M. Contraceptive vaccine formulations with sperm proteins. In: Bronson R A, Alexander N J, Anderson D J, Branch D W, Kutteh W H, eds. *Reproductive Immunology*. Mass. Blackwell Science. part 2, chapt. 33, 1996.
24. Haas G G Jr, Bronson R A, D'Cruz J, Fusi F M. Antisperm antibodies and infertility In: Bronson R A, Alexander N J, Anderson, D J, Branch D W, Kutteh W H, eds. *Reproductive Immunology*. Mass. Blackwell Science. part 2, Chapt. 7, 1996.
25. Rodman T C, Pruslin F H, To S E, Winston R, Allfrey V G. Turnover of basic chromosomal, proteins in fertilized eggs: a cytoimmunochemical study of events in vivo. *J Cell Biol* 90:351–361, 1981.
26. Monchev S, Tsanev S. Protamine-histone replacement and DNA replication in the male mouse pronucleus. *Mol Reprod Devel* 25:72–76, 1990.
27. Fleet J C. A new role for lactoferrin: DNA binding and transcription activation. *Nutr Rev* 53:226–231, 1995.
28. Garre C, Bianchi-Scarra G, Sirito M, Musso M, Ravazzolo R. Lactoferrin binding sites and nuclear localization in K562 (s) cells. *J Cell Physiol* 153:477–482, 1992.
29. Hutchens T W, Henry J F, Yip T T, Hachey D L, Schanler R J, Motil K J, Garza C. Origin of intact lactoferrin and its DNA-binding fragment found in the urine of milk-fed infants. Evaluation of stable isotopic enrichment. *Ped Res* 29:243–250, 1991.
30. Concar D, The jaws of lactoferrin. *Nature* 344:710, 1990.
31. Gerstein M, Andersen B F, Norris G E, Baker E N, Lesk A M, Clothia C. Two hinges produce a see-saw motion between alternative close-packed interfaces. *J Mol Biol* 234:357–372, 1993.
32. Baker E N, Anderson B F, Baker H M, Day C L, Rumball S V, Smith C L, Thomas D H. Three dimensional structure of lactoferrin in various functional states. *Adv Exp Med Biol* 357:1–12, 1994.
33. Lonnerdal B, Iyer S, Lactoferrin: molecular structure and biological function. *Ann Rev Nutr* 15:93–110, 1995.

EXAMPLE 3

Production of RWT-4 and RWT-12 Hybridoma Cell Lines

Each of the hybridomas was prepared by fusion of a human umbilical cord blood B cell with a myeloma.

Myeloma fusion partner for RWT-4 was a heteromyeloma produced by fusion of a mouse and a human myeloma cell, obtained from ATCC: 5HMD33.

Myeloma fusion partner for RWT-12 was HMMA. (Posner, M. R. et al., *Hybridoma* 6:611, 1987).

For each hybridoma, umbilical cord blood B cells were obtained and immortalized as described above in Example 1.

After five weeks, the culture medium of each well was tested by ELISA for reactivity with Tat protein. The media of selected cultures of those EBV-immortalized cells was then tested with each of the peptides (shown in Example 5, FIG. 5). Three of those displaying reactivity only with peptide 4 (SEQ ID NO: 4) (and at lower levels with peptide 5, SEQ ID NO: 5) and three displaying reactivity only with peptide 8 (SEQ ID NO: 8) (and at lower level with peptides 7, 9 (SEQ ID NO: 7, 9)) were selected for fusion with the respective fusion partner as described above in Example 1. Note correction to that procedure: the fused cells (representing the hybridomas) were plated out at 0.5 cells per well to assure that no more than one cell) was seeded into a well, thus assuring monoclonality.

The cells were grown in NY/HT (Sigma), supplemented with 20% fetal calf serum, SPIT (Sigma) and Pen/Strep, to a density of $10^6$ cells/ml, and spun at 400 RPM, 5 min.

Each pellet was suspended in medium, consisting of 80% fetal calf serum, 10% DMSO and 10% RPMI-1640, and stored, in 2 ml aliquots, at 70° C. or in liquid nitrogen. Those aliquots represent the hybridomas RWT-4 and RWT-12 deposited with ATCC on Feb. 12, 1998 and Feb. 25, 1998, respectively.

EXAMPLE 4

Testing of Specific Reactivity of Hybridoma Cell Lines RWT-4 and RWT-12

The culture medium of each, containing the specific IgM monoclonal antibody secreted by the hybridoma, was treated for recovery of the antibody.

The medium was concentrated in a CENTRICON® C-100 (available from Millipore of Bedford, Mass.) column to remove salt and all proteins of mol. wt. less than 100 Kd. The concentrated solution was then passed through a size exclusion gel on a Pharmacia S-300 column. The first peak of eluate was run on SDS polyacrylamide gel to inspect purity, demonstrated by display of two bands, representing the light and the heavy chain of the specific IgM, and no other bands. The eluate was then reconcentrated in a new column to 200 µg/ml.

The light chain of each Mab was identified by ELISA with peroxidase labelled anti-gamma and anti-kappa.

The heavy chain (epitope specificity) of each was identified by ELISA with the set of peptides.

| LIGHT CHAIN IDENTIFICATION | | | |
|---|---|---|---|
| ELISA : | 1. unlabeled rb > IgM | | |
| | 2. Mab or total hu IgM (Sigma) | | |
| | 3. perox. labeled anti-kappa or anti-lamda | | |
| Perox Labelled Anti-Lambda | 0 ab | Total IgM | RWT-4 Mab |
| 1:4k | 01 | .24 | .73 |
| 1:6k | 01 | .16 | .54 |
| 1:10k | 0 | .12 | .37 |
| Anti-Kappa | | | |
| 1:4k | 04 | .55 | .06 |
| 1:6k | 01 | .36 | .04 |
| 1:10k | 0 | .23 | .02 |

-continued

LIGHT CHAIN IDENTIFICATION

Conclusion: light chain for RWT-4 is lambda

| Anti-Lambda | 0 ab | Total IgM | RWT-12 Mab |
|---|---|---|---|
| 1:4k | 02 | .89 | .03 |
| 1:6k | 01 | .65 | .02 |
| 1:10k | 07 | .45 | .01 |
| Anti-Kappa | | | |
| 1:4k | 04 | >1.00 | .80 |
| 1:6k | 03 | .83 | .57 |
| 1:10k | 02 | .56 | .39 |

Conclusion: light chain for RWT-12 is kappa

EPITOPE DETERMINATION IN TERMS OF TAT PEPTIDE SPECIFICITY

| | ST | RWT-4 Mab | RWT-12 Mab |
|---|---|---|---|
| Pep 1 | .01 | .03 | .05 |
| 2 | .02 | .02 | .04 |
| 3 | .03 | .01 | 0 |
| 4 | .48 | .94 | .02 |
| 5 | .20 | .35 | .12 |
| 6 | .07 | .01 | .07 |
| 7 | .16 | .07 | .36 |
| 8 | .12 | .07 | .42 |
| 9 | 0 | .02 | .01 |
| 10 | 0 | .01 | .03 |
| 11 | 0 | 0 | 0 |
| 12 | .33 | .16 | .72 |
| Total Tat Protein | .49 | .55 | .44 |

Peptide 12 (here) is designated peptide 8 in Example 5, FIG. 6. Therefore,

| here | FIG. 2 |
|---|---|
| 7 | 7 |
| 12 | 8 |
| 8 | 9 |
| 9 | 10 |
| 10 | 11 |
| 11 | 12 |
| 12 | 8 |

Dilutions: ST serum 1:100
Mab's 1 μl/ml of the hybridoma cells

These data represent the average, for each antibody/antigen reaction, of 20 separately run assays.

EXAMPLE 5

In the present Example, the following materials and methods were used.

Sera

Human

The 70 HIV+ and 70 HIV− sera reported in FIG. 6 were collected prior to 1994, and assayed for reactivity with Tat protein. Therefore the characteristics of the HIV+ cohort are not attributable to the anti-HIV medications in use since that time. Of those 70 HIV+ sera, 52 were available for the epitope analysis of Table I in which were included 8 additional HIV+ sera for a total of 60 sera from HIV+ individuals not on medication. The sera for the HIV+ serial sets (FIGS. 9, 10, 11) were aliquots of specimens submitted for clinical examination with clinical data and concurrent medication noted. The 80 normal (HIV−) sera of Table I were assembled from specimens submitted for pre-employment examination identified only by age, gender and "no clinical findings", and from donations by laboratory personnel.

Chimpanzees

A total of 22 sera from adult chimpanzees, certified as normal, were obtained: 16 (7 ♂, 9 ♀) from YERKES Regional Primate Center (Emory University); 6 (2 ♀, 4 ♂) from LEMSIP (NYU Medical Center). Serum of 1 ♂ and 1 ♀ of the latter group were collected 22 months and 10 months, respectively, post innoculation with HIV infected cells.

Monkeys

A total of 32 sera from normal monkeys were obtained: 20 rhesus macaques from YERKES, 1 from LEMSIP and 2 from LARC (Laboratory Animal Research Center, Rockefeller University), 4 pig tail macaques and 5 baboons from LARC. Also, serum was obtained from 1 of the rhesus macaques following innoculation with SIV (Mac 239) infected cells and 2 specimens of rhesus plasma, 6 months post-innoculation with cell free supernatant of SIV Mac 239 culture, were obtained from Dr. Lingi Zhong (Aaron Diamond AIDS Research Center, Rockefeller University).

Rabbits

Sera obtained from 20 (10 ♂, 10 ♀) New Zealand white rabbits (prior to any treatment) were generously provided by James Nolan (Hospital for Special Surgery, New York) and 10 were obtained from LARC. 1 specimen of rabbit serum post-immunization with HIV Tat protein was obtained from Intracel Corp (Isaquah, Wash.)

Mice

Sera from 30 normal adult mice: 12 Balb C, 6 C57 black, 2 MRL-lpr, and 10 Swiss Webster were obtained through LARC. A series of 3 immunizations with HIV Tat protein/adjuvant was administered to 1 Balb C and 1 Swiss Webster and adjuvant alone was administered to 1 Balb C and 1 Swiss Webster. Sera included in the data of Table I represent the specimens collected 16 weeks after the final innoculation of each mouse.

Antigens

Recombinant Tat protein was obtained from Intracel Corp. in lyophylized form. Reactivity and working dilution for each vial of the protein was standardized with a single (standard) human serum (16). Tat peptides (SEQ ID NOS: 1 to 12) (FIG. 5), representing overlapping sequences in accordance with the published amino acid alignment of HIV Tat (17) were prepared as previously described (14). The most recent review (26) confirms that Tat is a highly conserved HIV protein with little digression from that sequence displayed by the various HIV clades.

Elisa

All sera were stored at −70° C. in small aliquots, to minimize the effects of repeated freeze-thaw. The ELISA protocol has been rigidly standardized and statistically evaluated (e.g. 15,16). Each serum/antigen was tested in a minimum of 3 separate assays. The corrected serum O.D. for each antigen represented the read-out O.D. of the serum/antigen minus the O.D. of serum background (0 antigen). Corrected O.D. of 0.10 was considered positive. If corrected O.D. was 0.08–0.15, the assay was repeated 3 additional times. For assay of human and chimp sera, a single standard serum (ST) was included on each titer plate and the final titer was calculated as X/ST. Peroxidase labeled anti-human IgG or IgM (KPL) was used for all human and chimpanzee sera. Anti-monkey IgM or IgG (KPL) was found to be non-reactive with chimpanzee sera, but was appropriate by all criteria of specificity and serum-dilution proportionality with the different monkey sera tested. Similarly, the anti-mouse IgM or IgG (Sigma) and anti-rabbit IgM or IgG (KPL) were screened for specificity and dilution related gradient of reactivity. Since the peroxidase labeled antibodies for each species were derived from goat serum, the ELISA included an extra blocking step, i.e. 1% normal goat serum applied following the antigen wash and prior to application of the species-specific test serum, to assure that no part of the displayed reactivity was attributable to goat antibodies.

TABLE 1

| Species | # of Sera | IgM Peptide: 1 | 4 | 8 | Tat | IgG 1 | 4 | 8 | Tat |
|---|---|---|---|---|---|---|---|---|---|
| Humans | | | | | | | | | |
| Males | 40 | 0 | 40 | 38 | 40 | 0 | 38 | 31 | 38 |
| Females | 40 | 0 | 40 | 40 | 40 | 1 | 40 | 36 | 40 |
| HIV + | 60 | 0 | 60 | 46 | 60 | 1 | 60 | 21 | 60 |
| Chimps | | | | | | | | | |
| Males | 11 | 0 | 11 | 10 | 11 | 0 | 11 | 9 | 11 |
| Females | 11 | 0 | 11 | 11 | 11 | 0 | 11 | 8 | 11 |
| HIV + | 2 | 0 | 2 | 2 | 2 | 0 | 2 | 2 | 2 |
| Simmians | | | | | | | | | |
| Monkeys | 32 | 0 | 0 | 0 | 0 | 0 | 32 | 2 | 21 |
| SIV + | 3 | 0 | 0 | 0 | 1 | 0 | 3 | 3 | 3 |
| Rabbits | | | | | | | | | |
| Normal | 30 | 0 | 2 | 0 | 0 | 0 | 3 | 0 | 0 |
| Tat + | 1 | 1 | 0 | 0 | 1 | 1 | 1 | 0 | 1 |
| Mice | | | | | | | | | |
| Normal | 30 | 0 | 0 | 0 | 0 | 0 | 2 | 0 | 1 |
| Adj. Only | 2 | 0 | 0 | 0 | 0 | 0 | 0 | 0 | 0 |
| Tat + | 2 | 0 | 0 | 0 | 0 | 2 | 0 | 0 | 2 |

Results

Human

Figure 6A:
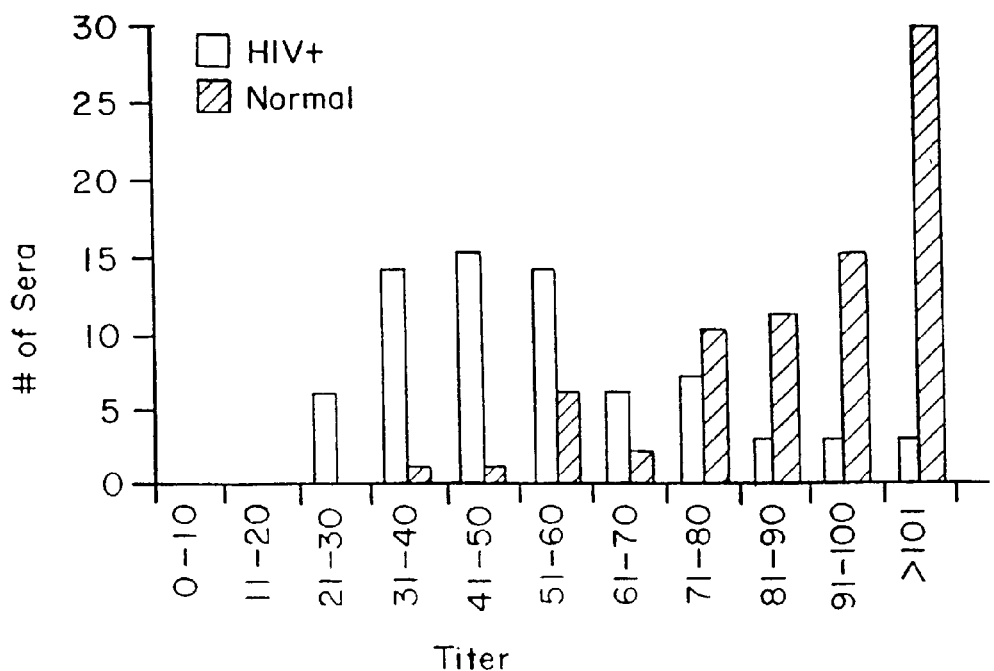
FIG. 6(A and B).
Figure 6B:
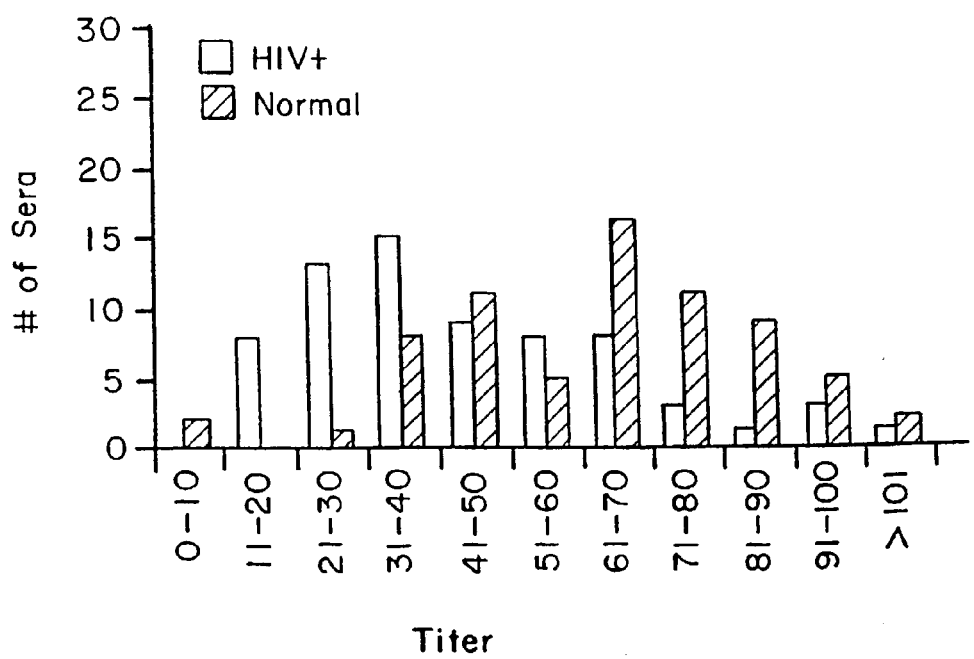

FIG. 6 presents the assay data of IgM and IgG reactivity with Tat protein of HIV+ and HIV− (normal) sera. As noted in METHODS, those HIV+ sera were collected from individuals who had not received any anti-HIV medication other than that in general use prior to mid-1994 (e.g. AZT). Comparison of the assembly of titers of the two cohorts of 70 sera each, shows that the IgM titers (FIG. 6A) of the HIV+ cohort are at significantly lower levels than those of the HIV− cohort. The distribution of the Tat-reactive IgG titers of the same sera (FIG. 6B), however, appears to be random, both with respect to comparison of the two cohorts and, in individual sera (not shown), in relation to the Tat-reactive IgM titers. Those IgG titers may represent maturation forms of the natural antibodies (27,28) or antibodies independently induced by unrelated antigens with sequences sufficiently concordant with regions of Tat protein to be reflected as Tat-reactive.

Figure 9A:
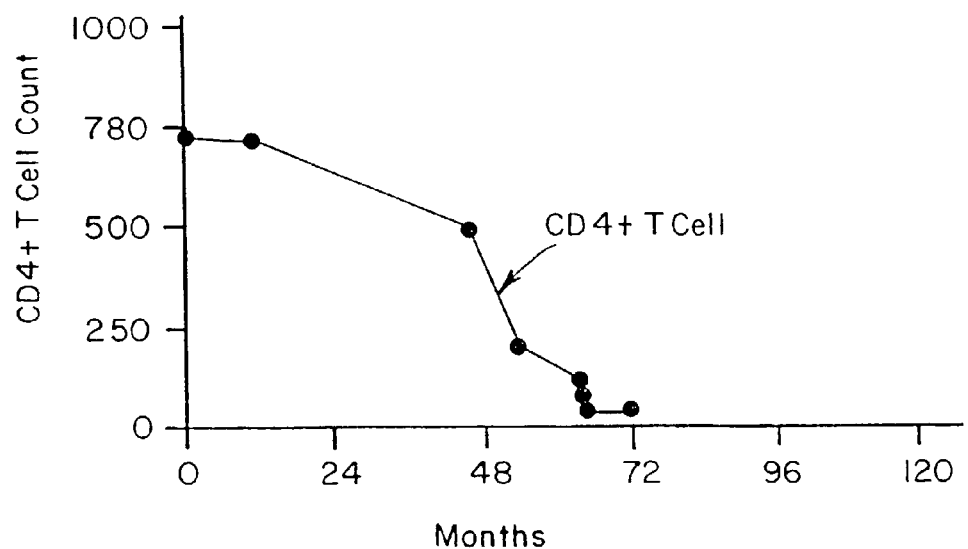
Figure 9B:
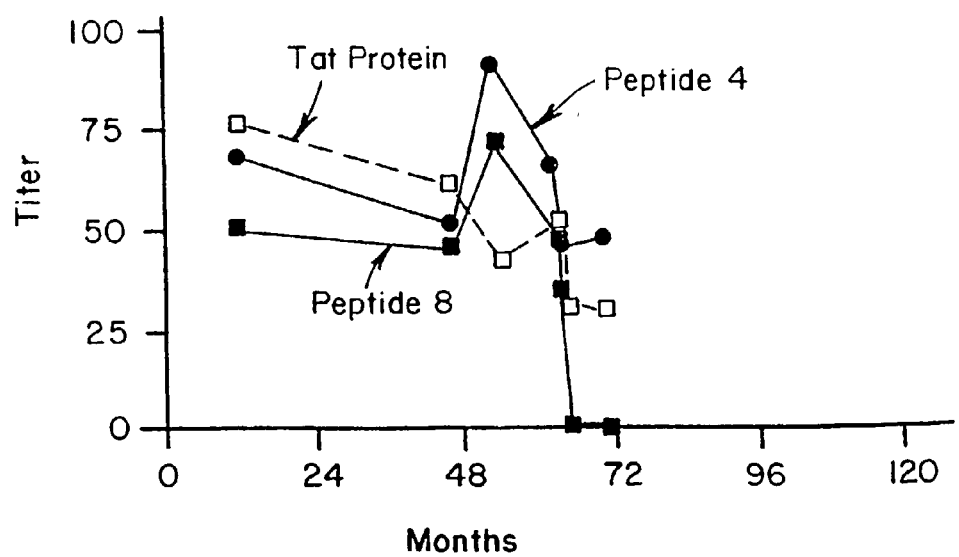
Figure 10A:
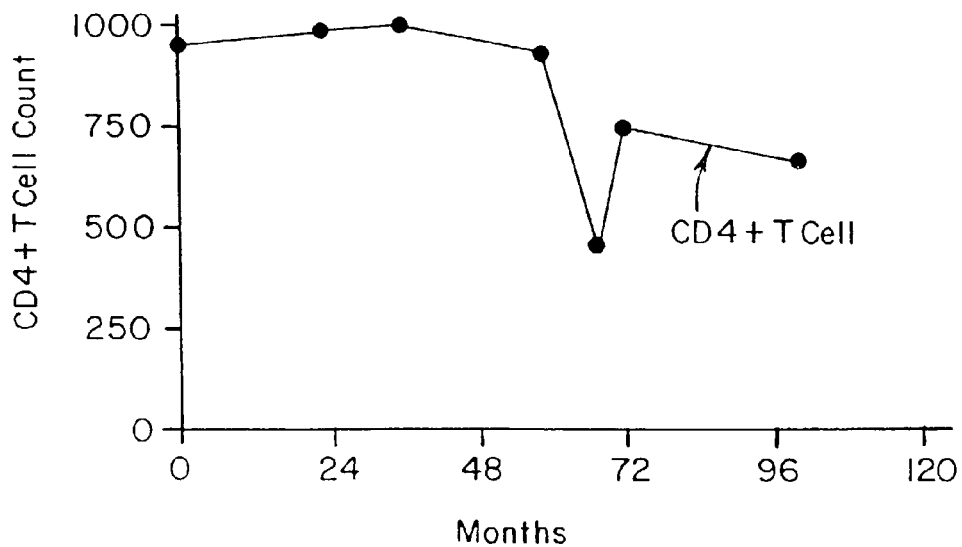
Figure 10B:
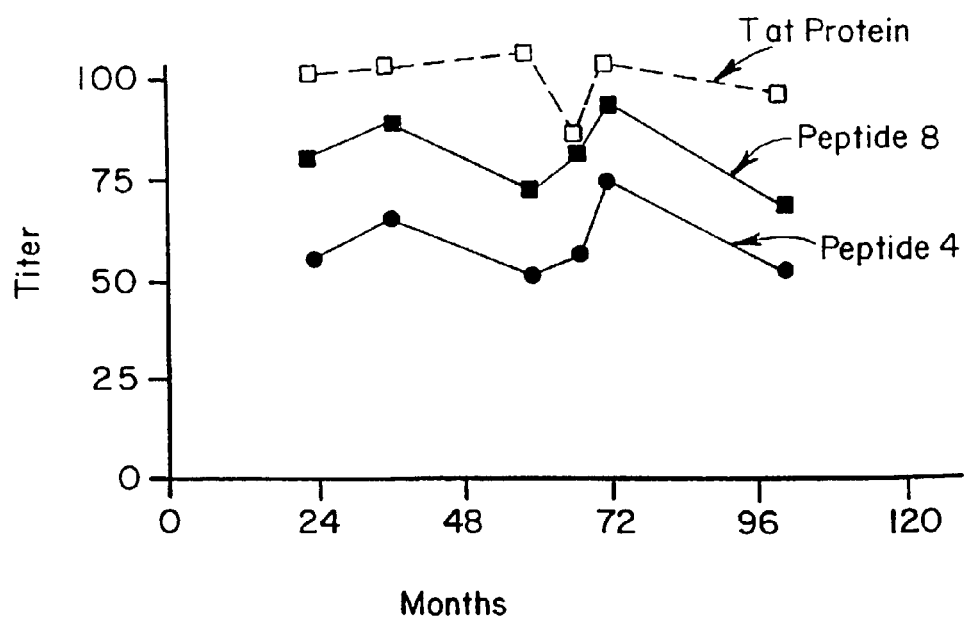

Epitope analysis (Table I) of sera of each of the two human cohorts shows that the entire IgM reactivity with Tat protein is limited to two non-adjacent sequences: one including peptides 4,5 embracing the cysteine-rich region and the other peptides 7,8,9 representing the arginine rich region (FIG. 1). In accord with the data of Table I, all (80) HIV− (normal) males and females have significant titers of IgM reactive with Tat protein as well as with the epitope represented by peptide 4 (SEQ ID NO: 4), while all but 2 have significant titers with that represented by peptide 8 (SEQ ID NO: 8). All of the 60 HIV+ sera have low, but significant, titers of IgM antibodies reactive with Tat protein and the sequence represented by peptide 4 (SEQ ID NO: 4), while only 46 of the 60 have IgM reactive with the arginine-rich sequence represented by peptide 8 (SEQ ID NO: 8). For even those HIV+ sera that are within the range of positive, the IgM reactivities with peptide 8 (SEQ ID NO: 8) are at low levels (FIG. 7), clearly suggestive of a trend to depletion, more so than that of peptide 4 (SEQ ID NO: 4) (FIG. 8). Again, the IgG antibodies (Table I) may be considered to represent maturation forms (27, 28) of the IgM natural antibodies and/or those independently induced by some exogenous antigenic factor. The latter is probably applicable to the IgG reactive with peptide 1 (SEQ ID NO: 1) (FIG. 5), present in one HIV− serum, therefore not Tat induced, and one HIV+ serum (Table I). The data of FIGS. 7 and 8 confirm that the decline of the Tat reactive natural antibodies is more stringently reflected in that reactive with peptide 8 (SEQ ID NO: 8) (FIG. 7) than in that reactive with peptide 4 (SEQ ID NO: 4) (FIG. 8). The correlation of the titers of Tat reactive IgM natural antibodies with the pathoprogression of HIV and with the CD4+ T cell count, an established index of that progression (29), is shown in FIGS. 9, 10, 11. Each is a display of data obtained from serial specimens of a single individual, including IgM assay titers for Tat protein, peptide 4 (SEQ ID NO: 4), peptide 8 (SEQ ID NO: 8) and clinical laboratory report of CD4+ T cell counts. The series in FIG. 9 is that from an HIV+ male collected over a period of five years preceding his death with a diagnosis of AIDS. Each value for Tat protein IgM titer reflects the combination of the peptide 4 (SEQ ID NO: 4) and peptide 8 (SEQ ID NO: 8) IgM values for the same specimen. Particularly striking is the sharp rise followed by the precipitous drop in the peptide 8 (SEQ ID NO: 8) reactivity concurrent with the virtual wipe-out of the CD4+ T cells in the specimen collected 8 months prior to death. FIG. 10 is a display of data of the series of specimens from an HIV+ male whose duration of infection is estimated at over 11 years and who has had no anti-HIV medication and no symptoms of HIV pathogenesis and, thus, fits the criteria of long-term-survivor (LTS) or long-term-non-progressor (LTNP) (12,13). The pattern of maintenance of titers of the IgM natural antibodies reactive with Tat protein, peptide 4 (SEQ ID NO: 4) and peptide 8 (SEQ ID NO: 8) are similar to those defined for normal (HIV−) humans (14,16). The high levels of titers, particularly those for peptide 8 (SEQ ID NO: 8), are correlative with the maintenance of CD4+ T cell counts within the normal range. Similar correlation is shown in the series of specimens (FIG. 7) from a single HIV+ individual for whom antiviral therapy was initiated following report of decline in CD4+ T cell count. Following a period of medication, both CD4+ T cell count and the titers of the natural antibodies, particularly those reactive with peptide 8 (SEQ ID NO: 8), rose. The following successive specimens showed maintenance of both CD4+ T cell counts and antibody titers in the normal range, concomitant with a general state of wellness of the patient.

Chimpanzee

The sera of all of the 22 normal chimps (Table I) had significant titers of both IgM and IgG antibodies reactive with Tat protein and peptide 4 (SEQ ID NO: 4). For peptide 8 (SEQ ID NO: 8), 21 of that group displayed significant IgM and 17 displayed significant IgG reactivity. The sera of each of the 2 HIV inoculated chimps displayed significant IgM and IgG reactivity with Tat protein, with the sequences represented by peptides 4 (SEQ ID NO: 4) and 8, (SEQ ID NO: 8) and with no other. Thus, the natural antibody repertoire of chimpanzee is similar to that of humans.

Monkey

No IgM reactive with Tat protein or any of its constituent peptides was detected in the sera of any of the 32 normal sera (Table I). Of the 3 SIV infected monkeys, one showed reactivity with Tat protein. All 32, however, displayed IgG reactivity with peptide 4 (SEQ ID NO: 4) and 21 of those displayed IgG reactivity with Tat protein. Two sera of the normal macaques and all three of the SIV infected macaques displayed IgG reactivity with peptide 8 (SEQ ID NO: 8).

Rabbit

Of the 30 normal rabbit sera, two displayed IgM reactivity with peptide 4 (SEQ ID NO: 4) which, however, was not accompanied by detectable IgM reactivity with Tat protein. Those two and an additional normal rabbit serum displayed IgG reactivity with peptide 4 (SEQ ID NO: 4) but, again, not with Tat protein. The Tat immunized rabbit serum displayed IgM reactivity with peptide 1 (SEQ ID NO: 1) and with Tat protein and IgG reactivity with peptide 4 (SEQ ID NO: 4) as well as peptide 1 (SEQ ID NO: 1) and Tat protein. That distribution suggests that the peptide 4 (SEQ ID NO: 4) IgM and IgG reactivity in both normal and Tat immunized rabbit serum reflects a response to an exogenous antigen that is not detectable in the assembled Tat protein. The IgM and IgG reactivity with peptide 1 (SEQ ID NO 1), displayed in the serum of the Tat immunized rabbit is attributable to induction by the immunogen since that peptide 1 (SEQ ID NO: 1) reactivity is reflected in comparably high reactivity with Tat protein.

Mouse

Of the sera from 30 normal, two Tat/adjuvant and two adjuvant/only immunized mice, none displayed IgM reactivity with Tat protein or any of the peptides (Table I). Two of the 30 normal mouse sera displayed IgG reactivity with peptide 4 (SEQ ID NO: 4) and the serum of another mouse displayed IgG reactivity with Tat protein. The sera of the two mice immunized with adjuvant/only displayed no reactivity while the sera of the two mice immunized with Tat/adjuvant displayed exceedingly high (>1.0) activity with peptide 1 (SEQ ID NO: 1) and with Tat protein. Clearly, for both rabbit and mouse, Tat protein is a potent inducer of an antibody response specifically directed to the sequence displayed in peptide 1 (SEQ ID NO: 1).

Discussion

The significance of the Tat protein is shown early in the pathogenetic sequence of HIV infection by its role in cell attachment and entry of the virus. Evidence from in vitro study indicates that Tat participates in viral internalization, mediated primarily by the basic domain (30,31), represented by Tat peptides 7, 8, 9 (SEQ ID NOS: 7, 8, 9) (FIG. 5). Intracellular propagation of the virus is also dependent upon Tat through its interaction with the Tar region of the viral RNA, resulting in transactivation (18, 19). The cysteine region of Tat, represented by Tat peptides 4,5 (SEQ ID NOS 4, 5) (FIG. 5) plays an essential role in Tat/Tar binding and the consequent replication of HIV (18,19). Thus, two activities of Tat—mediation of viral cell entry and activation of the internalized virus to replicate—are dependent upon the sequences of Tat that include the epitopes for the two natural IgM antibodies that are present in the sera of all human and chimpanzee sera examined in this study, but are not present in the sera of other mammals, e.g. monkeys, rabbits, mice (Table I)

In accord with that epitopic specificity, we propose that those natural antibodies provide, or contribute to, the human host mechanism of resistance to HIV pathogenesis in the early post-HIV infection period. Retardation of viral entry and intracellular replication by those antibodies in the human host and absence of that retardation in rhesus macaques may account for the observations that T lymphocyte turnover in SIV infected rhesus macaques occurs at a considerably higher rate than that in HIV infected humans (32,33). Although the precise mechanisms whereby the CD4+ T cell population is depleted in the peripheral blood cells of HIV+ humans are not yet specifically established, a relationship between the CD4+ T cell count and titers of the Tat-reactive natural antibodies is demonstrated in the serial specimens of FIGS. 9, 10, 11 of this study. In each series, the CD4+ T cell counts parallel the maintenance and drop of the antibody titers.

However, the providential arrest of Tat-related pathogenicity by those natural antibodies may be limited by the immune system recognition of the antibody-reactive sequences of Tat as self antigens and the consequent induction of tolerance (21, 22).

The separate and coordinate principles of innate and adaptive immunity have received much attention recently (6,7,8) which, hopefully, will provide further elucidation of the mechanisms and events of self recognition followed by tolerance. Thus far, the fundamental and implemental event of self tolerance appears to be that of deletion, or turning off, of the T and/or B cells involved in natural antibody production (23). Thus, as the Tat antigen load is increased, the production of Tat-reactive natural antibodies may be stifled, antibody-mediated restriction of the aggressive activities of Tat lost, and the period of pathoprogressive latency terminated. A pathogenic activity of Tat, well documented in vitro, is that of induction of apoptosis (29). The proposition that the Tat-reactive natural antibodies may impede the action of Tat, and thereby contribute to maintenance of the early period of apparent latency following HIV infection, is supported by the observation that persons designated LTS (long term survivor) (12) or LTNP (long term non progressor) (13) show little evidence of T cell apoptosis (21) and, as we have shown (FIG. 10), maintain normal levels of the natural antibodies. In correlation are reports (34) that the resistance of chimpanzees to progress to AIDS is accompanied by maintenance of T cell levels and little evidence of Tat induced apoptosis.

Although the mechanisms underlying depletion of T cells by apoptosis are not completely understood, recent studies have established that the Fas/Fas ligand system is not the modulating factor in HIV induced apoptosis of CD4+ T cells (35, 36). Particularly provocative, however, is a recent report that SIV (mac 239) induced apoptosis in peripheral blood mononuclear cells in vitro is mediated by the Fas/Fas ligand system (37). That difference between SIV and HIV in the mechanism of apoptosis mediation is critically relevant to the thesis of this study—that the interaction of HIV with the human immune system is significantly unique. Another significant difference between HIV and SIV is indicated by in vitro studies of the effect of intervention by interferon on viral replication. That effect appears to be primarily concerned with viral DNA synthesis which, in SIV infected cells, is blocked by interferon but, in HIV infected cells, is not (38).

Apoptosis of B cells as well as T cells has been attributed to action by Tat (29). Even more compelling are the accumulating reports of the involvement of Tat in the neurodegeneration leading to dementia (24). The reports have included Tat dose-dependent apoptosis of human fetal neurons in culture (39) and neuronal apoptosis detected in brain tissue from patients who had died with a diagnosis of AIDS (40). The probability that the neurotoxic effects of Tat demonstrated in vitro may occur in vivo is supported by the potential ability of Tat to permeate the blood brain barrier. Various analyses of the capacity for vascular permeability and blood brain barrier passage by the sperm chromosomal protein, protamine, have assigned that function to the arginine concentration of protamine (41). That same capacity is inherent in the arginine rich sequence of Tat, represented here by peptides 7,8,9 (SEQ ID NOS: 7, 8, 9) (FIG. 5). Of particular relevance is the epitope analysis for the human natural antibody reactive with Tat peptide 8 (SEQ ID NO: 8) which showed (16) that the epitope for that natural antibody is present in certain arginine-rich sequences of protamine as well as in HIV Tat protein.

The epitope similarity for the IgM and IgG for each of the two human natural antibodies suggests that each represents a pair of isotype of the same antibody. We have previously proposed that the constancy of IgM titers, but not the IgG titers, of the two natural antibodies in serial specimens, from each of a group of normal individuals, indicates that the IgM is the homeostasis-maintaining isotype (16). The mechanism and utility of class switch of natural antibodies are currently not well understood nor readily apparent but, hopefully, will be clarified in the course of current investigations of the molecular and functional aspects of the switch of isotype in innate as well as adaptive immunity (42).

Therefore, at present, assignment of separate roles to the IgM and IgG isotope of the human Tat reactive natural antibodies is not feasible. However, it is clear that, in HIV+ humans, Tat-reactive antibodies attributable to immunogenic induction do not occur (Table I). Since Tat-reactive antibodies are induced in monkeys, rabbits and mice (Table I), it appears that the failure is unique to the human immune system. Since chimpanzees are presumed to have high level of genetic identity with humans (20), attribution of that uniqueness to genetic specificity is supported by the profile of Tat reactive antibodies in the chimpanzee sera (Table I). The parallel with human sera is evident: pre and post HIV infected chimps have IgG and IgM antibodies reactive with Tat peptides 4 and 8 (SEQ ID NOS: 4 and 8) (FIG. 5) and with no other (Table I). However, the apparently greater innate resistance of chimps to the pathoprogression to AIDS than that of HIV+ humans (10, 11) may be a departure from the genetic identity, possibly in some immune system component participating in induction of tolerance (21, 22). The question then arises: is the same genetic characteristic related to the protection against the ravages of HIV with which LTS/LTNP are endowed (12, 13)?

REFERENCES FOR EXAMPLE 5

1. McCune, J. M. Animal models of HIV-1 disease. 1997. *Science* 279:2141.
2. Donahue, R. E., B. A. Burnell, M. C. Zinc, M. E. Metzger, R. P. Westro, M. R. Kirby, T. Unangst, J. E. Clements and R. A. Morgan. 1998. Reduction in SIV replication in rhesus macaques infused with autologous lymphocytes engineered with antiviral genes. *Nat. Med.* 4:181.
3. Hulskotte, E. G. J, A. M. Geretti, A. D. M. E. Osterhaus. 1998. Towards an HIV vaccine. *Vaccine* 16:904.
4. Heilman, C. A. and D. Baltimore. 1998. HIV vaccines—where are we going? *Nat. Med.* 4:532.
5. Almond, N. M. and J. L. Heeney. 1998. Aids vaccine development in primate models. *Aids* 12: (suppl.A) S133.
6. Janeway, C. R. Jr. 1998. Presidential address to the American Association of Immunologists. The road less traveled by: the role of innate immunity in the adaptive immune response. *J. Immunol.* 161:539.
7. Bendelac, A. and D. T. Fearon. 1997. Innate immunity. Innate pathways that control acquired immunity. *Curr. Opinion Immunol.* 9:1.
8. Carroll, M. C. and A. P. Prodeus. 1998. Limkages of innate and adaptive immunity. *Curr. Opinion Immunol.* 10:36.
9. Steinman, R. M. and R. N. Germain. 1998. Antigen presentation and related immunological aspects of HIV-1 vaccines. *AIDS* 12:(suppl.A) S97.
10. Ehret, A., M. O. Westendorp, I. Herr, K. M. Debatin, J. L. Heeney, R. Frank and P. H. Kramer. 1996. Resistance of chimpanzee T cells to human immunodeficiency virus type 1 Tat-enhanced oxidative stress and apoptosis. *J. Virol.* 10:6502.
11. Novembre, F. J., M. Saucier, D. C. Anderson, S. A. Klumpp, S. P. O'Neill, C. R. Brown 2nd, C. E. Hart, P. C. Guenther, R. B. Swenson and R. M. McClure. 1997. Development of AIDS in a chimpanzee infected with human immunodeficiency virus type 1 infected with human immunodeficiency virus type 1. *J. Virol.* 71:4086.
12. Cao, Y., L Qin, L. Zhabg, J. Safrit and D. D. Ho. 1995. Virologic and immunologic characterization of long-term survivors of human immunodeficiency virus type 1 infection. *New Eng. J. Med.* 332:201.
13. Montefiori, D. C., G. Pantaleo, L. M. Fonk, J. Y. Zhou, M. Bilska, G. D. Miralles, and A. S. Fauci. 1996. Neutralizing and infection-enhancing antibody responses to human immunodeficiency virus type 1 in long-term non-progressors. *J. Infect. Dis.* 173:60.
14. Rodman, T. C., F. H. Pruslin, S. E. To and R. Winston. 1992. Human immunodeficiency virus (HIV) Tat-reactive antibodies present in normal HIV-negative sera and depleted in HIV-positive sera Identification of the epitope. *J. Exp. Med.* 175:1247.
15. Rodman, T. C., S. E. To, H. Hashish, and K. Manchester. 1993. Epitopes for natural antibodies of human immunodeficiency virus (HIV)-negative (normal) and HIV-positive sera are coincident with two key functional sequences of HIV Tat protein. *Proc. Natl. Acad. Sci. USA* 90:7719.
16. Rodman, T. C., S. E. To, Sullivan J. J. and R. Winston. 1997. Innate natural antibodies. Primary roles indicated by specific epitopes. *Human Immunol.* 55:87.
17. Frankel, A. D., S. Biancalana and D. Hudson. 1989. Activity of synthetic peptides from the Tat protein of human immunodeficiency virus type 1. *Proc. Natl. Acad. Sci. USA.* 86:7397.
18. Kuppuswamy, M., T. Subramanian, A. Srinivasan and G. Chinnadurai. 1989. Multiple functional domains of Tat, the transactivator of HIV-1, defined by mutational analysis. *Nucl. Acids Res.* 17:3551.
19. Cullen, B. R. 1991. Regulation of human immunodeficiency virus replication. *Ann. Rev. Microbiol.* 45:219.
20. Crouau-Roy, B., S. Service, M. Slatkin and N. Freimer. 1996. A fine-scale comparison of the human and chimpanzee genomes: linkage disequilibrium and sequence analysis. *Hum. Mol. Genet.* 5:1131.
21. Matzinger, P. 1994. Tolerance, danger and the extended family. *Ann Rev. Immunol.* 12:991.
22. Van Parijis, L. and A. K. Abbas. 1998. Homeostasis and self-tolerance in the immune system: turning lymphocytes off. *Science* 280:243.
23. Klein, L., T. Klein, U. Ruther and B. Kyewsaki. 1998. $CD^4$ T cell tolerance to human C-reactive protein, an inducible serum protein, is mediated by medullary thymic epithelium. *J. Exp. Med.* 188:5.
24. Chen, P., M. Mayne, C. Power and A. Nath. 1997. The Tat protein of HIV-1 induces tunor necrosis factor alpha production. Implications for HIV-associated neurologic diseases. *J. Biol. Chem.* 272:22385.

25. Herbein, G., C. Valint, J. L. Lovett and E. Verdin. 1998. Distinct mechanisms trigger apoptosis in human immunodeficiency virus type 1-infected and in uninfected bystander T lymphocytes. *J. Virol.* 72:660.
26. Korber, B., B. Foley, T. Leitner, F. McCutchan, B. Hahn, J. W. Mellors, G. Myers and C. Kruken. 1997. Human Retroviruses and AIDS. Theoretical Biology and Biophysics Group T-10. Los Alamos national Laboratory. Los Alamos, N. Mex.
27. Coutinho, A., M. D. Kazatchkine and S. Avrameas. 1995. Natural antibodies. *Curr. Opinion Immunol.* 7:812.
28. Parker, W., K. Lundberg-Swanson, Z. E. Holznecht, J. Lateef, S. A. Washburn, S. J. Braedhoeft and J. L. Platt. 1996. Isohemaglutinins and xenoreactive antibodies. Members of a distinct family of natural antibodies. *Human. Immunol.* 45:94.
29. Samuelsson, A., C. Brostrom, N. van Dijh, A. Sonneborg and F. Chiodi. 1997. Apoptosis of CD4 and CD19+ cells during human immunodeficiency virus type-1 infection—correlation with clinical progression, viral loas and loss of humoral immunity. *Virology* 238:180.
30. Frankel, A. D. and C. O. Pabo. 1988. Cellular uptake of the tat protein from human immunodeficiency virus. *Cell* 55:1189.
31. Vives, E., P. Brodin and B. Lebleu. 1997. A truncated HIV-1 Tat protein basic domain repidly translocates through the plasma membrane and accumulates in the cell nucleus. *J. Biol. Chem.* 272:16010.
32. Mohri, H., S. Bonhoeffer, S. Monard, A. S. Perelson and D. D. Ho. 1998. Rapid turnover of T lymphocytes in SIV infected rhesus macaques. Science 279:1223.
33. Rosenzweig, M., M. A. De Maria, D. M. Harper, S. Friedrich, R. K. Jain and R. P. Johnson. 1998. Increased rates of CD4+ and CD8+ T lymphocyte turnover in simian immunodeficiency virus-infected macaques. *Proc. Natl. Acad. Sci. USA.* 95:6388.
34. Gougeon, M. L., H. Lecoeur, J. Heeney and F. Boudet. 1996. Comparative analysis of apoptosis in HIV-infected humans and chimpanzees.; relation with lymphocyte activation. *Immunol. Lett.* 51:75.
35. Ghandi, R. T., B. K. Chen, S. E. Sraus, J. K. Dale, M. J. Lenardo and D. Baltimore. 1998. HIV-1 directly kills CD4+ T cells by a Fas-independent mechanism. *J. Exp. Med.* 187:1113.
36. Noraz, N., J. Gozlan, J. Corbeil, T. Brunner and S. A. Spector. 1997. HIV-induced apoptosis of activated primary CD4+ T lymphocytes is not mediated by Fas-Fas ligand. AIDS 11:1671.
37. Iida, T., T. Igarashi, H. Ichimura, T. Kwata, T. Shimada, D. Magamachi, S. Yonehara, J. Imanishi and M. Hayami. 1998. Fas antigen expression and apoptosis of lymphocytes in macaques infected with simian immunodeficiency virus strain mac. *Arch. Virol.* 143:717.
38. Taylor, M. D., M. J. Korth and M. G. Katze. 1998. Interferon treatment inhibits the replication of simian immunodeficiency virus at an early stage—evidence for a block between attachment and reverse transcription. *Virology* 241:156.
39. New, D. R., M. Ma, L. G. Epstein, A. Nath and H. A. Gelbard. 1997. Human immunodeficiency virus type 1 Tat protein induces death by apoptosis in primary neuron cultures. *J. Neurovirol.* 168.
40. Wessenlingh, S. L., K. Takahashi, J. D. Glass, J. C. McArthur, J. W. Griffin and D. E. Griffin. 1997. Cellular localization of tumor necrosis factor mRNA in neurological tissue from HIV-infected patients by combined reverse transcription/polymerase chain reaction in situ hybridization and immunohistochemistry. *J. Neuroimmunol.* 74:1.
41. Westergren, I. and B. B. Johansson. 1993. Altering the blood-brain barrier in the rat by intacarotid infusion of polycations: A comparison between protamine, poly-L-lysine and poly-Larginine. *Acta Physiol. Scand.* 149:99.
42. Medzhitov, R. and C. A. Janeway. 1997. Innate immunity: impact on the adaptive immune response. *Cur. Opinion Immunol.* 9:4.

What is claimed is:

1. A hybridoma cell line having Accession No. ATCC CRL-12431.

2. An isolated human IgM monoclonal antibody produced by the hybridoma of claim 1 wherein said antibody is immunoreactive with human lactoferrin present in human sperm heads.

3. The isolated IgM antibody of claim 2 wherein said antibody is the monclonal equivalent of a circulating natural IgM antibody.

4. The isolated antibody of claim 3 wherein said antibody is reactive with lactoferrin present in the protein coat of the human sperm head.

5. The hybridoma of claim 1 wherein said hybridoma is produced by fusing an Epstein Barr virus-transformed human umbilical cord cell with a mouse: human heteromyeloma cell.

* * * * *